United States Patent
Wolfe et al.

(10) Patent No.: US 11,514,397 B2
(45) Date of Patent: Nov. 29, 2022

(54) SAFETY, MANAGEMENT AND TRACKING OF HOSPITAL PHARMACY TRAYS

(71) Applicant: Inmar Supply Chain Solutions, LLC, Winston-Salem, NC (US)

(72) Inventors: David G. Wolfe, Wexford, PA (US); Spencer W. Allen, Wexford, PA (US); Anthony Melanson, Wexford, PA (US)

(73) Assignee: INMAR SUPPLY CHAIN SOLUTIONS, LLC, Winston-Salem, NC (US)

( * ) Notice: Subject to any disclaimer, the term of this patent is extended or adjusted under 35 U.S.C. 154(b) by 254 days.

(21) Appl. No.: 16/448,493

(22) Filed: Jun. 21, 2019

(65) Prior Publication Data

US 2019/0333008 A1 Oct. 31, 2019

Related U.S. Application Data

(63) Continuation of application No. 15/182,753, filed on Jun. 15, 2016, now abandoned.

(60) Provisional application No. 62/175,782, filed on Jun. 15, 2015.

(51) Int. Cl.
*G06Q 10/08* (2012.01)
*G07F 17/00* (2006.01)
(Continued)

(52) U.S. Cl.
CPC ....... *G06Q 10/087* (2013.01); *G06K 7/10861* (2013.01); *G06V 30/224* (2022.01); *G07F 17/0092* (2013.01); *G16H 20/13* (2018.01); *G16H 30/40* (2018.01); *G16H 40/20* (2018.01); *G06V 30/10* (2022.01)

(58) Field of Classification Search
CPC ...... G06Q 10/087; G16H 20/13; G16H 40/20; G16H 30/40; G07F 17/0092; G06K 9/18; G06K 7/10861; G06K 2209/01
See application file for complete search history.

(56) References Cited

U.S. PATENT DOCUMENTS 6,226,035 B1 5/2001 Korein et al.
7,823,778 B1 11/2010 Singh et al.
(Continued)

FOREIGN PATENT DOCUMENTS

WO 20140145048 A1 9/2014

OTHER PUBLICATIONS

Rogers et al.. U.S. Appl. No. 16/704,573, filed Dec. 5, 2019.

*Primary Examiner* — Robert A Sorey
*Assistant Examiner* — Kimberly A. Sass
(74) *Attorney, Agent, or Firm* — Allen, Dyer, Doppelt + Gilchrist, P.A.

(57) ABSTRACT

A computer-implemented system and method is disclosed for inventory management including an inventory machine, a medication tray, and at least one marker. A medication tray includes a plurality of compartments to receive medications and other items, where each compartment is designated as a receptacle for a specific item or type of item. A marker is provided for each item placed in a compartment, and insertion of a medication tray into an inventory machine enables components to scan for markers. The markers are configured to generate identifying data and other data related to an item upon being scanned by an imaging apparatus and processed by a decoder apparatus. The correct/incorrect location of items within a medication tray, among other information, is determined in an automated fashion as part of the computer-implemented inventory management system and method.

23 Claims, 19 Drawing Sheets

(51) Int. Cl.
    *G06K 7/10*     (2006.01)
    *G16H 20/13*     (2018.01)
    *G16H 40/20*     (2018.01)
    *G16H 30/40*     (2018.01)
    *G06V 30/224*     (2022.01)
    *G06V 30/10*     (2022.01)

(56) References Cited

U.S. PATENT DOCUMENTS

| | | |
|---|---|---|
| 3,060,249 A1 | 11/2011 | Bear et al. |
| 8,065,035 B2 * | 11/2011 | Ross .................. G07F 11/1657 |
| | | 700/224 |
| 2002/0035484 A1 | 3/2002 | Mccormick |
| 2007/0187183 A1 | 8/2007 | Saigh et al. |
| 2010/0039513 A1 | 2/2010 | Glickman et al. |
| 2012/0130534 A1 | 5/2012 | Wurm |
| 2013/0002795 A1 * | 1/2013 | Shavelsky ................ A61J 7/04 |
| | | 348/14.01 |
| 2013/0195326 A1 * | 8/2013 | Bear .................... A61J 7/0084 |
| | | 382/128 |
| 2013/0346261 A1 * | 12/2013 | Phillips .................. B25H 3/028 |
| | | 705/28 |
| 2014/0165614 A1 | 6/2014 | Manning et al. |
| 2014/0261883 A1 | 9/2014 | Dent et al. |
| 2014/0350720 A1 | 11/2014 | Lehmann et al. |
| 2015/0283036 A1 * | 10/2015 | Aggarwal ............... A61J 7/049 |
| | | 206/534 |

\* cited by examiner

CRASH-1 (Emergency Crash Cart)

Community Hospital
Processed By
John Doe 5/28/2015 10:46am

Please Place Patients Label Here

Expiration Date 6/9/2015

Metoprolol 1mg/ml 5ml - NET

| Pocket | Medication | Full Qty | Replacement Qty | Expiration Date |
|---|---|---|---|---|
| 1 | Lidocaine HCL Inj., USP, 2% (20 mg/ml) | 2 | | 6/19/2015 |
| 2 | Atropine Sulfate Inj., USP (0.1mg/ml) | 2 | | 6/19/2015 |
| 3 | Epinephrine Inj., USP 1mg (0.1mg/ml) | 2 | | 6/15/2015 |
| 4 | Calcium Chloride Inj., USP, 10% (100mg/ml) | 2 | | 8/16/2015 |
| 5 | Metoprolol 1mg/ml 5ml | 5 | | 6/9/2015 |
| 6 | Sodium Bicarbonate Inj., 50mEq (1 MEq/ml) 4.2 grams | 1 | | 9/2/2015 |
| 7 | Sterile Water 30ml | 6 | | 9/1/2015 |
| 8 | Amiodarone HCL 150mg (50mg/ml) | 7 | | 6/19/2015 |
| 9 | Saline Flush 10ml | 6 | | 8/12/2015 |
| 10 | Epinephrine Inj., 1:1000 (1mg/ml) | 4 | | 8/12/2015 |
| 11 | Cefazolin 1g 5ml | 6 | | 12/1/2015 |
| 12 | 0.9% Sodium Chloride Inj., USP 250 ml | 2 | | 6/9/2015 |

FIG. 12

SAFETY, MANAGEMENT AND TRACKING OF HOSPITAL PHARMACY TRAYS

CROSS-REFERENCE TO RELATED APPLICATIONS

This patent application is a continuation application of U.S. patent application Ser. No. 15/182,753 filed Jun. 15, 2016, which claims the benefit of U.S. Provisional Patent Application No. 62/175,785, filed on Jun. 15, 2015, the entire contents of both are hereby incorporated by reference.

FIELD OF THE INVENTION

The present disclosure relates generally to a system and method for inventory management of medications and, in particular, to a system and method for inventory management of medications related to imaging markers associated with items to be inventoried on hospital pharmacy trays.

BACKGROUND OF THE INVENTION

Medication trays are often used to provide a specific selection and quantity of medications for a particular medical use case, physician preference, and/or location. A given hospital may have multiple variations of medication trays in use, each varying in type, amount, and/or placement of medications within the medication tray. Consequently, hospital pharmacies can manage a large quantity of medication trays used throughout a facility.

One aspect of managing the medication trays may be replenishment and verification of the contents held by a medication tray when a portion of the medication tray is used and the tray is later returned to a pharmacy. This may entail accounting for recalled, expired, and/or soon-to-expire medication. An additional aspect of managing medication trays may include ensuring proper placement of items within a medication tray so that inadvertent use or administration of a medication does not occur.

Existing inventory systems and methods consist of a mix of paper recording through manual means, electronic recording, and/or radio-frequency identification ("RFID") identification/recording to aid pharmacy personnel in the replenishment and handling of medications. These inventory systems and methods can be cumbersome and/or error prone. Furthermore, such systems and methods can be expensive to implement and operate. They may also fail to provide comprehensive inventory tracking. For instance, such systems and methods may fail to account for proper placement of items within a medication tray. One of the reasons for these deficiencies is a failure to identify, track, and control individual items within a medication tray in an automated and accurate manner so as to adequately manage kind, count, and location of items placed therein. For instance, a manual processes for identifying proper placement of items within a medication tray and proper location of the trays themselves can lead to misplaced and unaccounted for items.

The present invention is directed toward overcoming one or more of the above-mentioned problems

SUMMARY OF THE INVENTION

The system may include an inventory machine, a medication tray, at least one marker, and a computer system. A medication tray may have a plurality of compartments to receive medications and other items (e.g., liquid dosages, syringes, ampoules, etc.). Each compartment can be designated, via computer coding for example, as a receptacle for a specific item or type of item, the data of which may be programmed into a computer device of an inventory management system. A marker may be provided for at least one item placed in a compartment, and insertion of a medication tray into an inventory machine can enable an inventory machine to scan a medication tray for markers. Markers may also be provided on a medication tray to identify and track a medication tray in addition to identifying and tracking items within a medication tray. Markers may be integral to an item and/or medication tray (e.g., imbedded on a package of an item) and/or added to an item and/or medication tray by a user as part of an inventory process. Markers may be configured to generate identifying data and other data related to an item upon being scanned by an imaging apparatus. A decoder apparatus may be used to decode the data for processing. In some embodiments, both an imaging apparatus and a decoder apparatus may be part of an inventory machine.

A user may insert a medication tray into an inventory machine to perform an inventory scan. Upon inventory scanning a medication tray, a computer device may identify an item within a medication tray, via a marker, and compare an actual location of an item with a designated receptacle-compartment for that item. A computer device can also acquisition and examine other related data embodied within a marker, such as expiration date, approaching expiration date, manufacturer information, etc. The data can be associated with other information that may be acquisitioned by a computer device of a computer system via a computer network, such as recall information, a patient update status, a change in prescription, etc. Results of an inventory scan and data comparisons may be displayed on a display screen via a user interface ("UI"), which may be an interactive UI and/or a graphical user interface ("GUI"). A user may then remove a medication tray and make appropriate changes to items and their locations within a medication tray. A medication tray may be inserted back into an inventory machine for a subsequent scan (which may be an intermediate scan of a series of scans). After the items are properly placed within a medication tray, no inconsistencies are detected by an inventory machine, and no information causing concern (e.g., expiration date lapsed, recall, etc.) is detected, a concluding scan (which may be the latest intermediate scan) may be performed to generate an inventory record and/or a comparison template for the next inventory scan of the medication tray.

Effectuating the scanning, performing the data comparisons, and/or generating the reports may be done automatically by a computer device. Alternatively, effectuating the scanning, performing the data comparisons, and/or generating the reports can be done by a computer device upon a command entered by a user via a UI. Additionally, a UI may be programmed to generate a tray display screen showing an image of a medication tray overlaid with indictors superimposed on the items. Each indictor may be a colored dot, text box, or other indicia that can be used to inform a user whether an item is within its proper place in the medication tray, along with other pertinent information. A UI may be programmed to generate additional display screens showing pertinent data and usage statistics and other status information related to items and medication trays.

A computer device may be programmed to generate reports related to items and medication trays. A computer device can be further programmed to generate reports automatically. Alternatively, a user may enter command inputs via a UI to cause a computer device to generate reports. Reports may include any of the information displayed on any of the display screens generated via the UIs. A user may modify and/or create report formats to display the type of information most beneficial for a particular application.

The scanning may be performed by imaging and decoder apparatuses that can be configured to obtain information from optical machine-readable data symbols. Optical machine-readable data symbols can be embodied in markers that have been placed on items. In some embodiments, markers may be 2-dimensional bar codes that can also be human readable. Imaging and decoder apparatuses may be included with an inventory machine and/or on a hand-held reader. With a hand-held reader, data collected may be transmitted to an inventory machine and/or computer device (wirelessly and/or non-wirelessly) for the data comparison and report generating operations. Hand-held readers may be used to, among other things, track a medication tray and/or items as they are transported throughout the hospital. In addition, or in the alternative, to the hand-held imaging and marker system, medication trays can be tracked using other tracking means, such as RFID tagging, real-time locating systems ("RTLS"), etc.

Obtaining information from markers optically may not only enable an inventory management system to perform inventory of items and/or medication trays, but it may also determine correct/incorrect location of medication tray and/or items within a medication tray in an automated fashion. Furthermore, an inventory process may be performed quickly, accurately, and/or without complex, costly, identification equipment. The inventory management system, used in conjunction with the inventory management method, can further provide users with an inventory management system that is easy to use and quickly assessable. Quickly ascertaining relative locations of items and their designated receptacle-compartments may be beneficial during emergency use of a medication tray. For example, ensuring proper placement of items with pre-determined fixed locations within a medication tray can enable healthcare workers to quickly acquire necessary medication when needed, especially in exigent circumstances. Ensuring proper placement of items with pre-determined fixed locations within a medication tray may further reduce the risk associated with inadvertent use or administration of medication. Thus, verification of the correct location of medications in the medication tray may improve safety as well as efficiency.

With some implementations determining the exact location of an item can be based on marker position within the image. A nominal plane can be established by which positions of items and/or markers can be measured relative to the established nominal plane. For example, if an item is located above the nominal plane, an image of it will appear off-set (to the left or right) as compared to an image of the same item that is located at the nominal plane. This can be due to parallax. This difference in apparent position can be used to determine actual position of items in the tray. For instance, markers can be of a fixed size, and a position of the marker relative to the nominal plane can cause an image of the marker to appear larger or smaller as compared to an image of the marker located at the nominal plane. These differences in apparent size can be used to determine the location of items.

As will be described in detail, the disclosed inventory management system can facilitate imaging and scanning markers on items within a container to determine an inventory status, including a location of items. The inventory management system can further facilitate imaging and scanning markers placed on items by a user and/or markers placed on items by a manufacturer. Markers may be alphanumeric text identifying an item, barcodes identifying an item, and/or barcodes that are Data Matrix codes. Some embodiments can include systems and methods that use an image of a marker to read a marker, capture images with a single imager, capture images with a linear array of imagers indexed across a container, capture images with a matrix of imagers, use multiple imagers to generate overlapping images, and/or include use of an overall container imager. Other embodiments can determine item status by presence/absence of a marker and determine item location by location of a marker. Further embodiments can generate a report of inventory status, which may include a location of an item. In at least one embodiment, a report of exceptions can be generated by comparing expected inventory status with actual locations of items, where an exception can be an identified discrepancy of an item's actual location as compared to its expected location.

In one form, the inventory management system includes at least one scanning device comprising at least one imaging apparatus configured to scan at least one object in part by capturing at least one image of the at least one object and convert the at least one image into digital image data; at least one tray having at least one compartment structured to receive at least one item; at least one marker associated with the at least one object, wherein the at least one object is at least one of the at least one item and the at least one tray, wherein each marker includes encoded pertinent data thereon; at least one decoder apparatus in connection with the at least one imaging apparatus to acquisition the encoded pertinent data embodied in the digital image data to generate decoded pertinent data; and a computer device including a processor in association with a non-transitory memory, the computer device configured to store and display at least one of the digital image data, the encoded pertinent data, and the decoded pertinent data for the at least one object. The computer device is programmed with at least one item-tray recipe for associating the at least one compartment and the at least one item with a designated receptacle-compartment so as to assign the at least one item to the at least one designated receptacle-compartment, the computer device programmed to display data, for each object, corresponding to the item-tray recipe, the digital image data, and the decoded pertinent data.

In another foul, the inventory management system includes a computer device including a processor in association with a non-transitory memory, the computer device programmed with an item-tray recipe; and an inventory machine in connection with the computer device. The inventory machine includes a housing with a medication tray receiver structured to receive a medication tray; at least one imaging apparatus to capture images of objects placed within the medication tray receiver and convert the images into digital image data; and a decoder apparatus to decode encoded pertinent data embodied in the digital data to generate decoded pertinent data. The computer device receives and processes the decoded pertinent data and generates display data comprising the decoded pertinent data and item-tray recipe data.

In a further form, an inventory management method is provided that includes creating a marker encoded with pertinent information; associating the marker with at least one of a medication tray and an item capable of being received within a compartment of the medication tray; identifying the compartment as a designated receptacle-compartment for the item; creating an item-tray recipe corresponding to kind, count, and location of the item within the medication tray and in accordance with the designated receptacle-compartment; placing the item in the compartment of the medication tray in accordance with the item-tray recipe; scanning the medication tray with a scanning device, the scanning device comprising at least one imaging apparatus and at least one decoder apparatus; reviewing the pertinent information, an operational parameter of the scanning device, information related whether the item is in the assigned designated receptacle-compartment, tracking information, and/or status information; using at least the pertinent information for auditing and/or quality control; using the medication tray to conduct delivery operations and/or dissemination of the item; performing additional scanning for further auditing and/or quality control; and reviewing updated pertinent information, an updated operational parameter of the scanning device, updated information related whether the item is in the assigned designated receptacle-compartment, updated tracking information, and/or updated status information for replenishment, removal, restocking, and/or replacement of the item and/or the medication tray. Further embodiments include comparing an apparent size of the marker shown in the at least one image with the actual size of the marker to determine a position of the marker relative to a nominal plane.

While the disclosed systems and methods of inventory management are described as being related to inventory of medications, they are certainly not limited to such applications. Any process of inventorying items that may benefit from imaging markers associated with the items being inventoried may be applicable.

While these potential advantages are made possible by technical solutions offered herein, achieving them is not required. The presently disclosed system and method can be implemented to achieve technical advantages, whether or not these potential advantages, individually or in combinations, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIGS. 11A and 11B are exemplary tray display screen displays that may be generated by an inventory management system;

FIGS. 11C and 11D are exemplary item-recipe compare screen displays that may be generated by an inventory management system;

FIG. 11E is an exemplary medication tracking screen display that may be generated by an inventory management system;

FIG. 12 is an exemplary report that may be generated by an inventory management system;

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Inventory Machine

Figure 1:
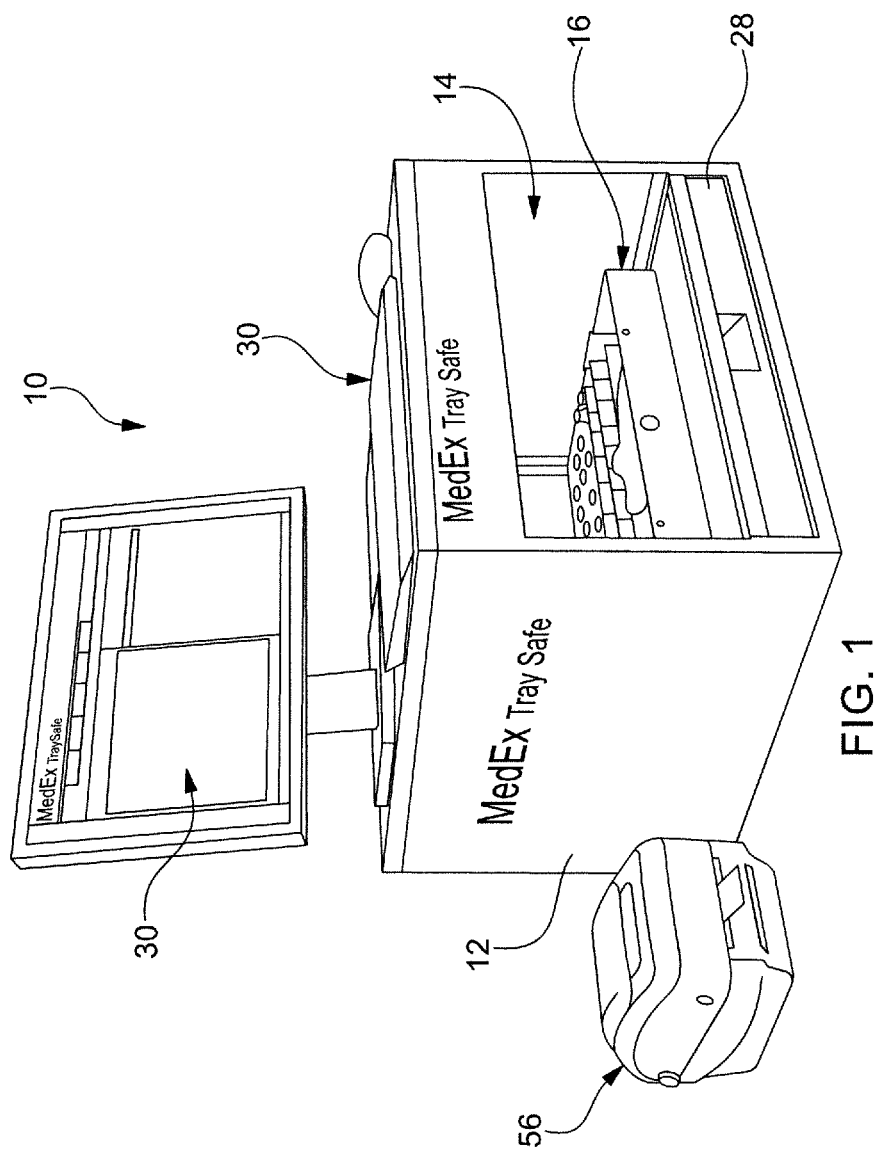
FIG. 1 is an exemplary inventory machine with a medication tray that may be used with an inventory management system.
Figure 2:
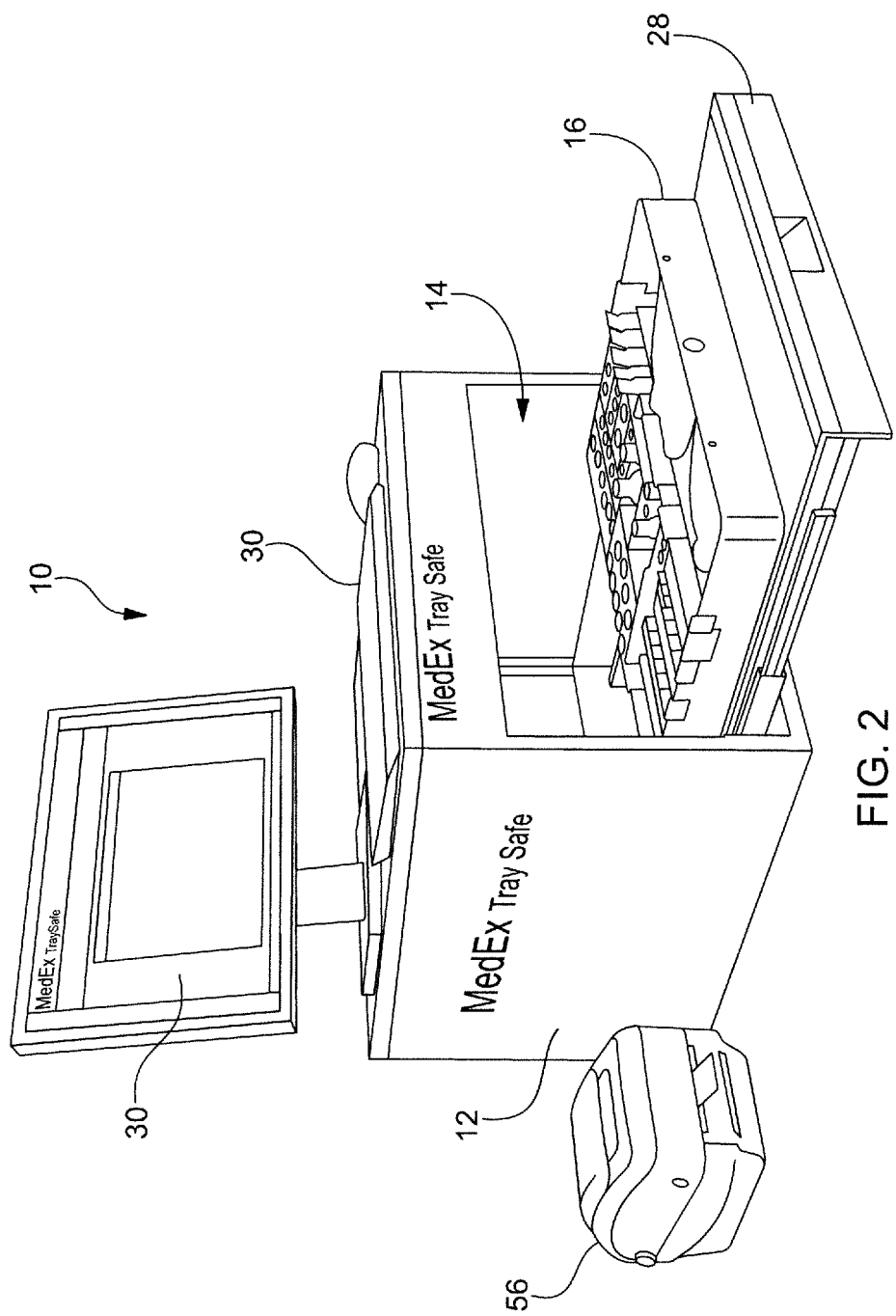
FIG. 2 is an exemplary inventory machine of FIG. 1 with a shelf in an extended position.
Figure 3A:
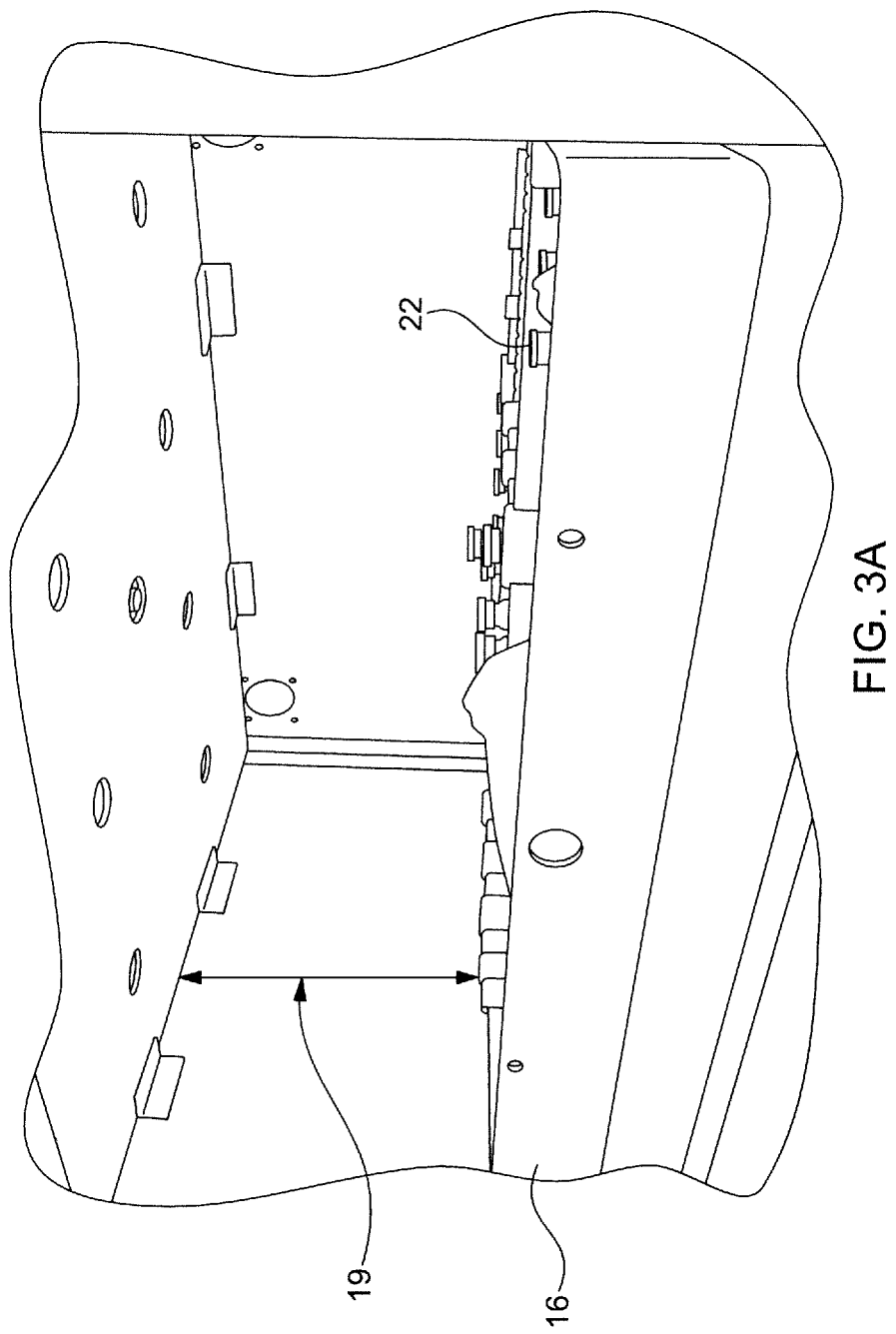
FIGS. 3A, 3B, and 3C are a view of an inside portion of a medication tray receiver, an imaging apparatus array, and another view of an inside portion of a medication tray receiver, respectively, that may be used with an inventory management system.
Figure 3B:
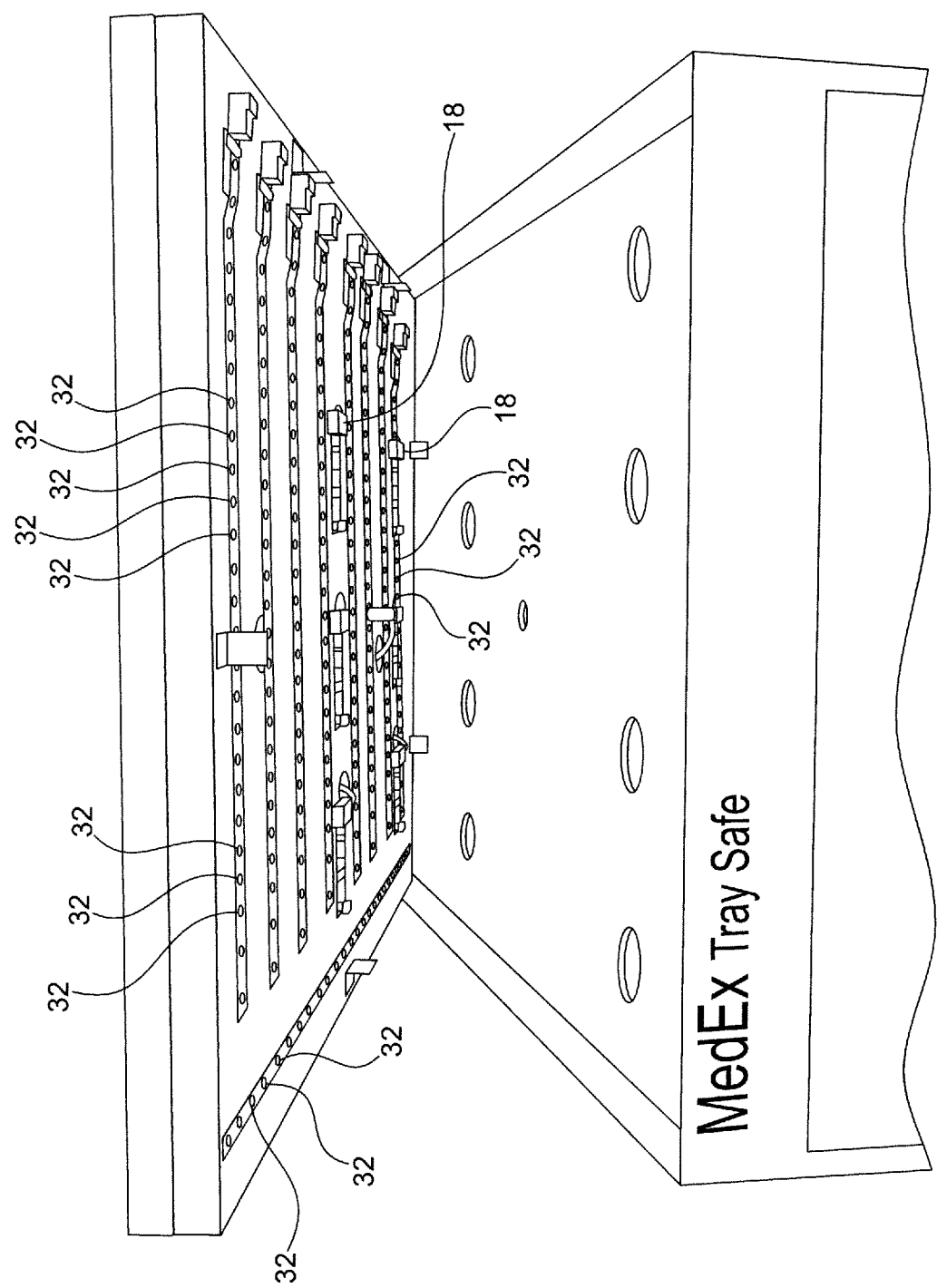

Referring to FIGS. 1-3, an inventory machine 10 can include a housing 12 with a medication tray receiver 14, where a medication tray 16 may be inserted into a medication tray receiver 14 for scanning. Within a portion of an inventory machine receiver 14 can be at least one imaging apparatus 18 and at least one decoder apparatus 20. When a medication tray 16 is inserted into a medication tray receiver 14, an imaging apparatus 18 can be used to perform a scan by capturing images of a medication tray 16 and its contents. Contents of a medication tray 16 may be items 22 placed within a medication tray 16 and held within compartments 24, for example, unlidded compartments, of a medication tray 16. For example, an item 22 may be medication placed within a designated compartment 24 of a medication tray 16, for example, by way of placement through an open upper end of the designated compartment. Captured images can be converted to digital data by a processor. A processor 112 may be programmed to perform conversion of images to digital data via application software stored on a non-transitory memory 114 associated with the processor 112. For example, a processor 110 may be a computer device 110 in connection with a computer system 100 associated with an inventory management system (see FIG. 14). Alternatively, a processor 112 may be some other hardware device, which may include a computer device 110, incorporated within an inventory machine 10. A decoder apparatus 20 may be used to acquisition pertinent data embodied in a marker 26 by processing digital data. In some embodiments, decoders 20 can be used to generate digital data of captured images. Pertinent data may be data corresponding to an item 22 and/or a medication tray 16 that a marker 26 is associated with. Pertinent data may include, but are not limited to, type of medication, actual location information, designated receptacle-compartment information, production data of a medication, manufacturer data of a medication, patient information associated with a medication, insurance information associated with a medication and/or a patient, delivery information, usage information, expiration date information, soon-to-expire information, medication recall information, regulatory compliance information, etc.

A hand-held reader (not shown) can be used in the alternative or in addition to an inventory machine 10. A hand-held reader may also include at least one imaging apparatus 18. A hand-held reader may also include a decoder apparatus 20. Alternatively, a hand-held reader may transmit, encoded data to an inventory machine 10, where a decoder 20 of an inventory machine 10 can perform the decoding. In either case, a hand-held reader can be in communication (wirelessly and/or non-wirelessly) with an inventory machine and/or a computer device of a computer system so that pertinent data may be transferred for processing by an inventory management system. For example, a hand-held reader may be in connection with an inventory machine 10 and/or a computer device of a computer system via hardwire and/or a wireless connection. A hardwire connection can be achieved via a Universal Serial Bus ("USB") cable, other data cable, coaxial cable, T1 cable, or other network cable. A wireless connection can be achieved via a transmitter, a receiver, and/or a transceiver unit, which may be in connection through a communications network of a computer system. In some embodiments, an inventory machine 10 and/or a hand-held reader can be computer devices that are part of a computer system.

An inventory machine 10 may be structured as a partially closed cabinet, properly sized to contain at least one medication tray 16. Each medication tray 16 can be received and retained within a medication tray receiver 14. It is contemplated for an imaging apparatus 18 to be located above an inserted medication tray 14 so that each medication tray receiver 14 would be configured to exhibit enough headroom 19 (a distance between an imaging apparatus and a top portion of the medication tray), accommodating at least one imaging apparatus 18 and an inserted medication tray 16 (see FIGS. 3A-3C).

A medication tray receiver 14 may include at least one shelf 28 configured to enable slidable motion of a medication tray 16 within an inventory machine 10. This may include slidable motion into and out from an inventory machine 10. For example, a medication tray 16 to be processed may be slid into an inventory machine 10 to be fully disposed within the confines of an inventory machine 10 (see FIG. 1) and slid out from an inventory machine 10 to be completely removed from an inventory machine 10 (see FIG. 2). Each shelf 24 may be configured to maintain convenient access for inserting, removing, and manipulating a medication tray 16. In some embodiments, a medication tray receiver 14 and/or a shelf 28 can include guides and/or mechanical stops to ensure that an inserted medication tray 16 is properly positioned and/or seated for effective scanning.

In alternative embodiments, a shelf 28 can be repositionable to enable adjustment of the headroom 19. This may be done to accommodate different size medication trays 16 and/or different size items 22 placed within the medication trays 16 (e.g., an item 22 may protrude above a top portion of a medication tray 16). This may also be done to adjust a focal length, field of view ("FOV"), and/or angles of incidence for an imaging apparatus 18. Adjustment of the headroom 19 may be performed manually by inserting a shelf 28 within an individual guide channel disposed within a medication tray receiver 14. Additionally, or in the alternative, adjustment of the headroom 19 may be performed automatically by incorporation of a shelf adjustment actuator that causes a shelf 28 to traverse a track upon actuation. An example of a shelf adjustment actuator may be a worm gear assembly associated with an encoder and a processor, where a processor may be programmed to receive inputs from an encoder and cause the worm gear assembly to actuate and force a shelf 28 to traverse a guide channel. A computer device of a computer system may be used to provide additional inputs to the processor from a user via a user interface ("UI") 30 and/or via algorithms programmed to auto-focus an imaging apparatus or improve other aspects of imaging and/or scanning by adjustment of the headroom 19.

Figure 3C:
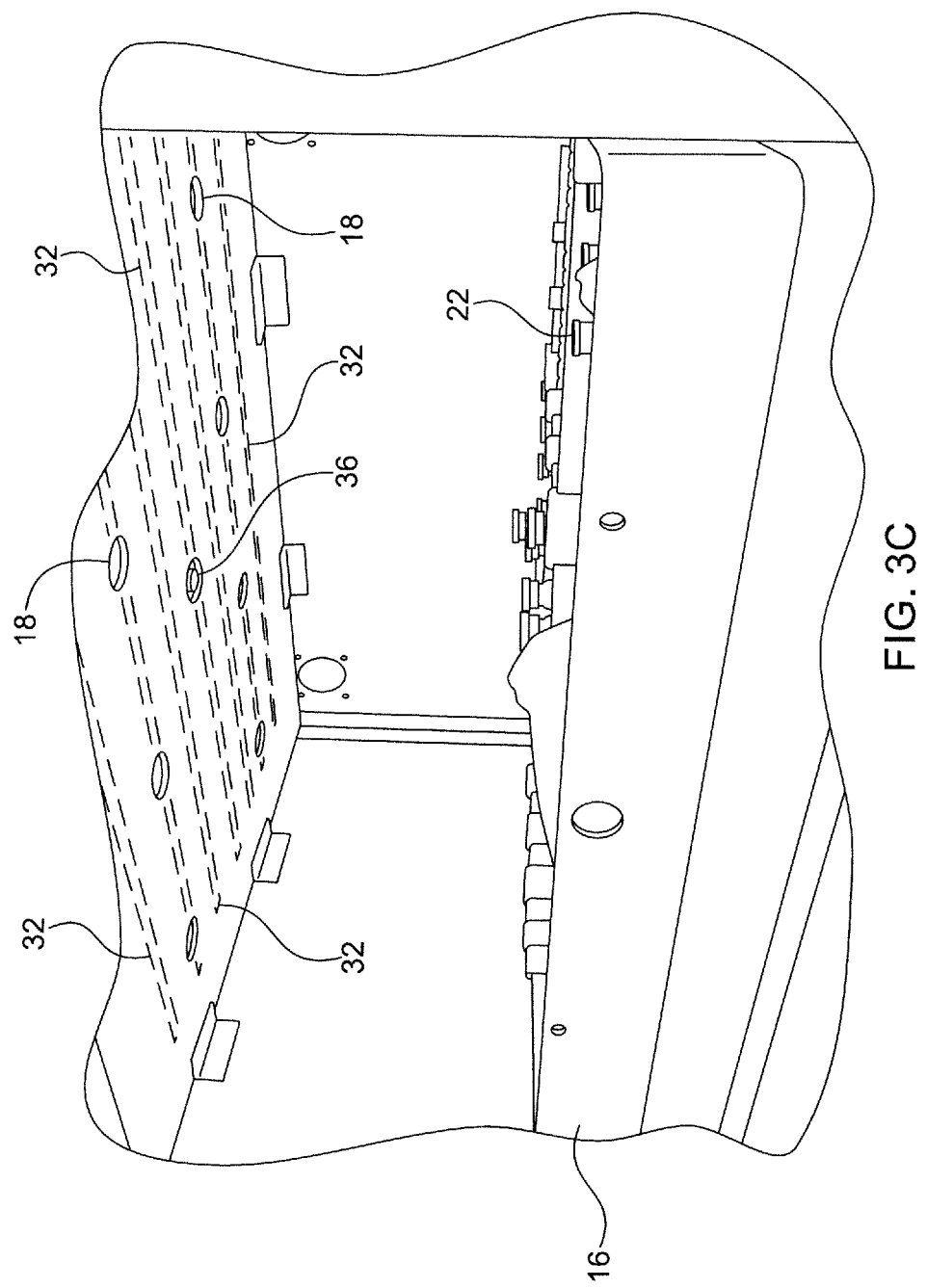
Figure 4:
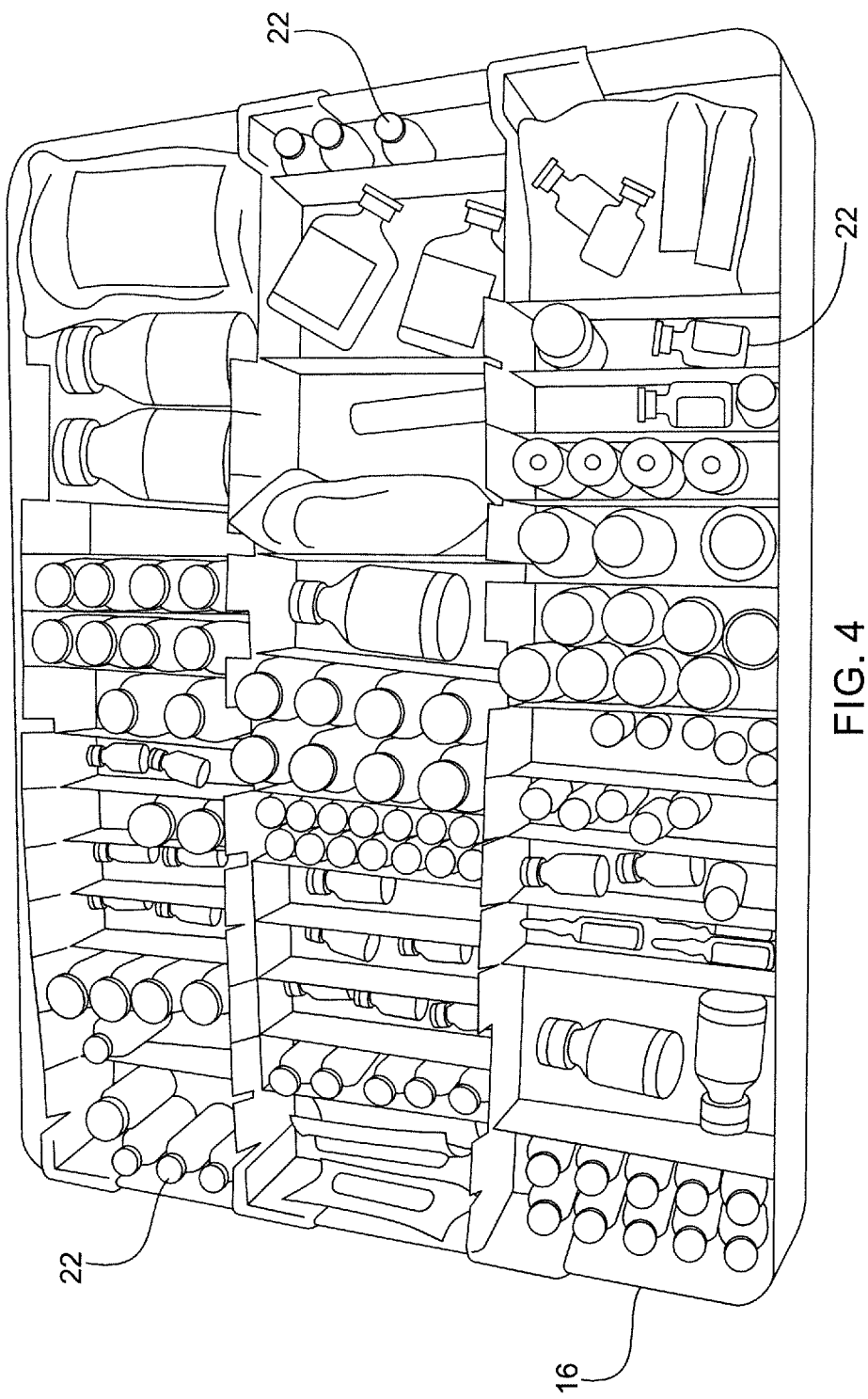
FIG. 4 is a medication tray.

As seen in FIG. 3C, the inventory machine 10 may be provided with at least one illumination source 32, which may be a light emitting diode ("LED"). Other illumination sources 32 may be used; however, a low power illumination source generating uniformly distributed lighting with low heat emission may be desired. Intensity, wavelength, amplitude, and other aspects may be controlled to generate a salutary illumination exposure environment for image capture and data decoding by an imaging apparatus 18 and a decoder apparatus 20. An illumination source 32 may be arranged in a fixed array or other assortments, as well as be controlled in various ways (brightness, frequency, pulsation, color, emission direction, angle, lateral and/or vertical displacement, etc.) to generate a desired light exposing environment.

Computer System

Figure 14:
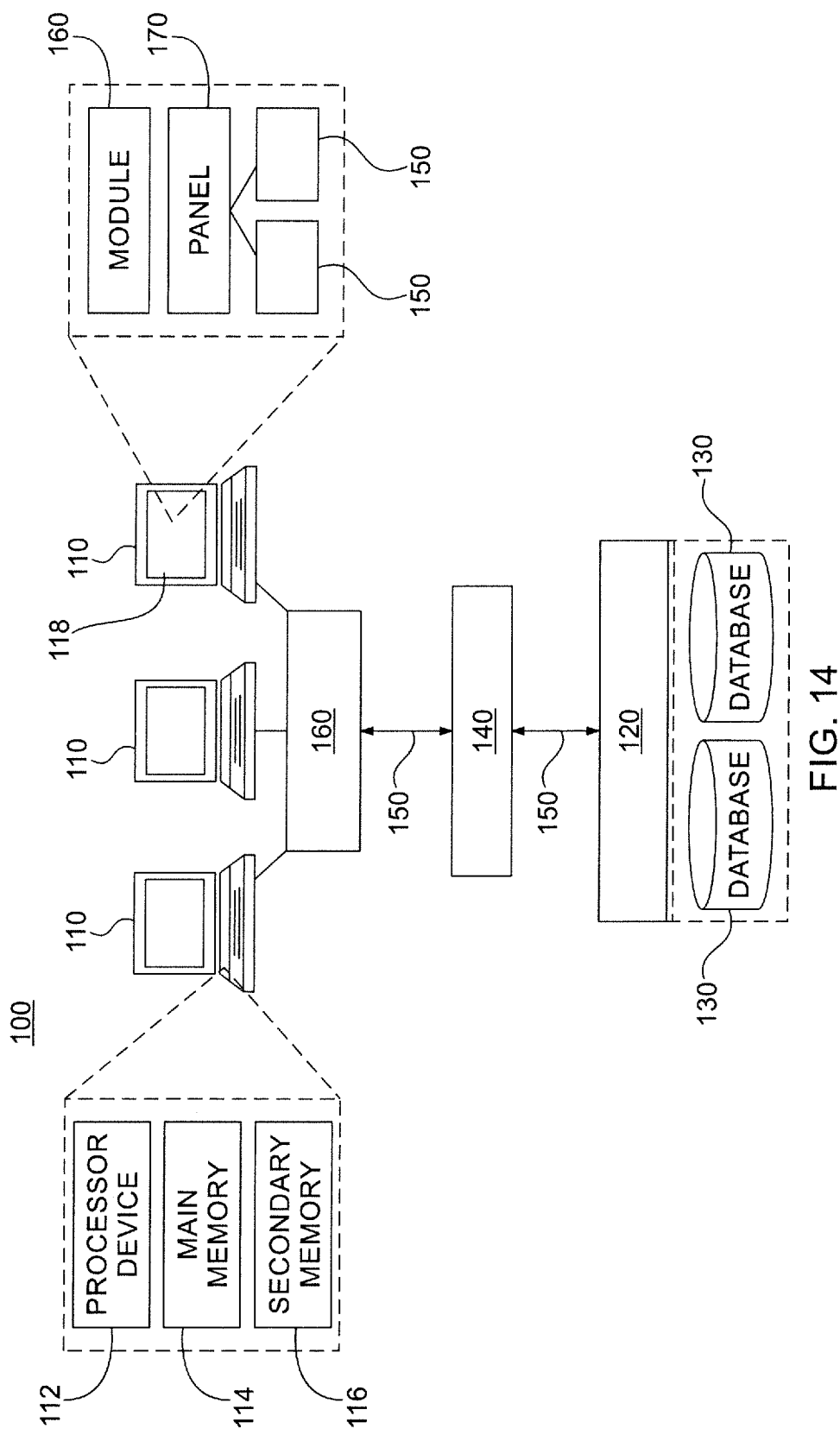

Referring now to FIG. 14, an exemplary computer system 100 that may be used with an inventory management system 10 is disclosed. Pertinent data acquisitioned from an inventory machine 10, a hand-held reader, and any other computer device of a computer system may be transmitted to a computer system 100 to be acquisitioned by a processor device 112 and manipulated by software, generating functional aspects programmed into a UI 30, which may be an interactive UI and/or a graphical user interface ("GUI"). A processor device 112 may be a computer device 110 in communication with a computer system 100. The computer device 110 can include a display monitor 118 to display screen displays of a UI 30.

A computer system 100 may include a plurality of computer devices 110, computer servers 120, databases 130, communication networks 140, and communication path/connections 150. A user of an inventory management system 10 may use at least one processor device 112, memory storage 114, and communications interface 160 to communicate and execute commands. Each computer server 120 may be connected to at least one database 130, where application software executed by each computer device 110 may cause processors 112 and other hardware devices to carry out functions of storing, coalescing, configuring, and transmitting data. Application software may be stored on any type of suitable computer-readable medium or media. This may be a non-transitory computer-readable medium or media, such as a magnetic storage medium, optical storage medium, or the like.

Wherever a user is referenced in this disclosure, it is understood that this reference can include associated computer device(s) 110, computer server(s) 120, database(s) 130, and/or uses thereof. Distributed communication networks may be used to enable connection and communication between each computer device 110. Each computer device 110 may communicate in whole, or in part, via web-sites through a communication network 140, which may include a web-server. Interactions between a user, computer devices 110, and a computer system 100 may be implemented using hardware, software, firmware, non-transitory computer readable media having instructions stored thereon, or a combination thereof, and may be implemented in a single or multiple of computer systems 100 or other processing systems. Hardware, software, or any combination thereof may embody modules and components used to execute functions of a computer system.

If programmable logic is used, such logic may execute on a commercially available processing platform or a special purpose device. Embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device 112 and a memory 114 may be used to implement the herein described embodiments.

A processor device 112 may be a single processor, a plurality of processors, or combinations thereof. Processor devices 112 may have one or more processor cores. The terms computer program medium, non-transitory computer readable medium, and computer usable medium may refer to tangible media, such as, for example, a removable storage unit and a hard disk installed in a hard disk drive. A processor device 112 may be a special purpose or a general purpose processor device. A processor device 112 may be connected to a communication infrastructure. A communication infrastructure may include, but is not limited to, a bus, message queue, network, multi-core message-passing scheme, etc.

A computer device 110 of a computer system may include a main memory 114. A main memory 114 may include, but is not limited to, a random access memory, a read-only memory, etc. The computer system 100 may include a secondary memory 116. A secondary memory 116 may include, but is not limited to, a hard disk drive, a removable storage drive, a floppy disk drive, a magnetic tape drive, an optical disk drive, a flash memory, etc. Any of the main and the secondary memories may be a non-volatile memory. A removable storage drive may read from and/or write to a removable storage unit. A removable storage unit may include a removable storage media that may be read by, and written to, a removable storage drive. For example, if a removable storage drive is a floppy disk drive, a removable storage unit may be a floppy disk. A removable storage unit may be non-transitory computer readable recording media. In some embodiments, a secondary memory 116 may include alternative means for allowing computer programs or other instructions to be loaded onto a computer device 110 of a computer system 100. This may be, for example, a removable storage unit and/or an interface. Examples of such means may include, but are not limited to, a program cartridge and cartridge interface (e.g., as found in video game systems), a removable memory chip (e.g., Electronic Erasable Readable Programmable Read-Only Memory ("EEPROM"), Programmable Read-Only Memory ("PROM")) and associated socket, and/or other removable storage units and interfaces.

A computer system 100 may include a communications interface 160. A communications interface 160 may be configured to allow software and data to be transferred between a computer system and external devices. Communications interfaces 160 may include, but are not limited to, a modem, a network interface (e.g., an Ethernet card), a communications port, Personal Computer Memory Card International Association ("PCMCIA") slot and card, etc. Software and data transferred via a communications interface 160 may be in a form of signals, which may be electronic, electromagnetic, optical, or other signals. Signals may travel via a communications path 150, which may be configured to carry signals and may be implemented using wire, cable, fiber optics, a phone line, a cellular phone link, a radio frequency link, etc.

Computer program medium and computer usable medium may refer to memories, such as a main memory 114 and a secondary memory 116, which may be memory semiconductors (e.g., Dynamic Random-Access Memory ("DRAM")). These computer program products may be means for providing software to a computer network of the system 100. Computer programs (e.g., computer control logic) may be stored in a main memory and/or a secondary memory. Computer programs may also be received via a communications interface 160. Such computer programs, when executed by a processor device, may enable a computer system 100 to execute commands and act upon the various components of an inventory management system 10. Accordingly, such computer programs may represent controllers of a disclosed computer system 100. Where the present disclosure is implemented using software, the software may be stored in a computer program product and loaded into a computer system using a removable storage drive, an interface, a hard disk drive, and/or a communications interface 160.

A computer device 110 may be a processor, a microprocessor, minicomputer, server, mainframe, laptop, personal data assistant, wireless email device, cellular phone, smartphone, pager, fax machine, scanner, or any other programmable device configured to enable transmission and/or reception of data, which may be over a network. A computer device 110 may include a peripheral device, such as an input/output device. A peripheral device may include, but is not limited to, a keyboard, a mouse, a screen display, a touch screen, a pen, a monitor, a printer, a hard disk drive, a floppy disk drive, a joystick, an image scanner, etc.

One or more electronic computer networks 140 may be utilized by the computer system 100 to promote communication among different components, transfer data, and/or share resource information. Such computer networks 140 may be embodied as, but not limited to, at least one of Ethernet, wireless Local Area Network ("LAN"), Mobile Area Network ("MAN"), Wide Area Network ("WAN"), Virtual Private Network ("VPN"), Storage Area Network ("SAN"), Global Accelerator Network ("GAN"), Home Phoneline Network Alliance ("HomePNA"), etc.

A computer system 100 may comprise a processor 112 that may be operatively associated with at least one module 160, which may be programmed to display panels 170 and/or screen displays 180 on a computer device monitor. The processor 112 may be programmed to execute computer-readable instructions included within a module 160. Computer-readable instructions may be in a form of application software stored on a non-transitory computer readable medium operatively associated with a processor 112. Each module 160 may be configured to generate a GUI and/or other UI 30 enabling at least one user to issue commands, access data stored on a data storage media operatively associated with the processor 112, and/or transmit data to and from the data storage media. A module 160 may include software, firmware, hardware, or any reasonable combination thereof.

A module 160 may be programmed to display at least one panel 170. A panel 170 may be programmed to display information and grant access to data related to certain aspects and functionalities of an inventory management system 10. Through the various modules 160 and panels 170, a computer system 100 can provide a communication network 140 to orchestrate interaction between a user, a computer system 100, and the various components of an inventory management system 10. For instance, different panels 170 of each module 160 may be programmed to facilitate differentiated display of information and differentiated interaction between users, components of a computer system 100, and components of an inventory management system 10.

Various embodiments of the present disclosure can be described in terms of an example computer system 100 described above; however, other embodiments of a computer system 100, along with other embodiments of computer architectures, can be used. Although operations may be described as a sequential process, some of the operations may be performed in parallel, concurrently, and/or in a distributed environment, and with program code stored locally or remotely for access by single or multi-processor machines. In some embodiments, the order of operations may be rearranged without departing from the spirit of the disclosed subject matter.

Medication Tray

Figure 5:
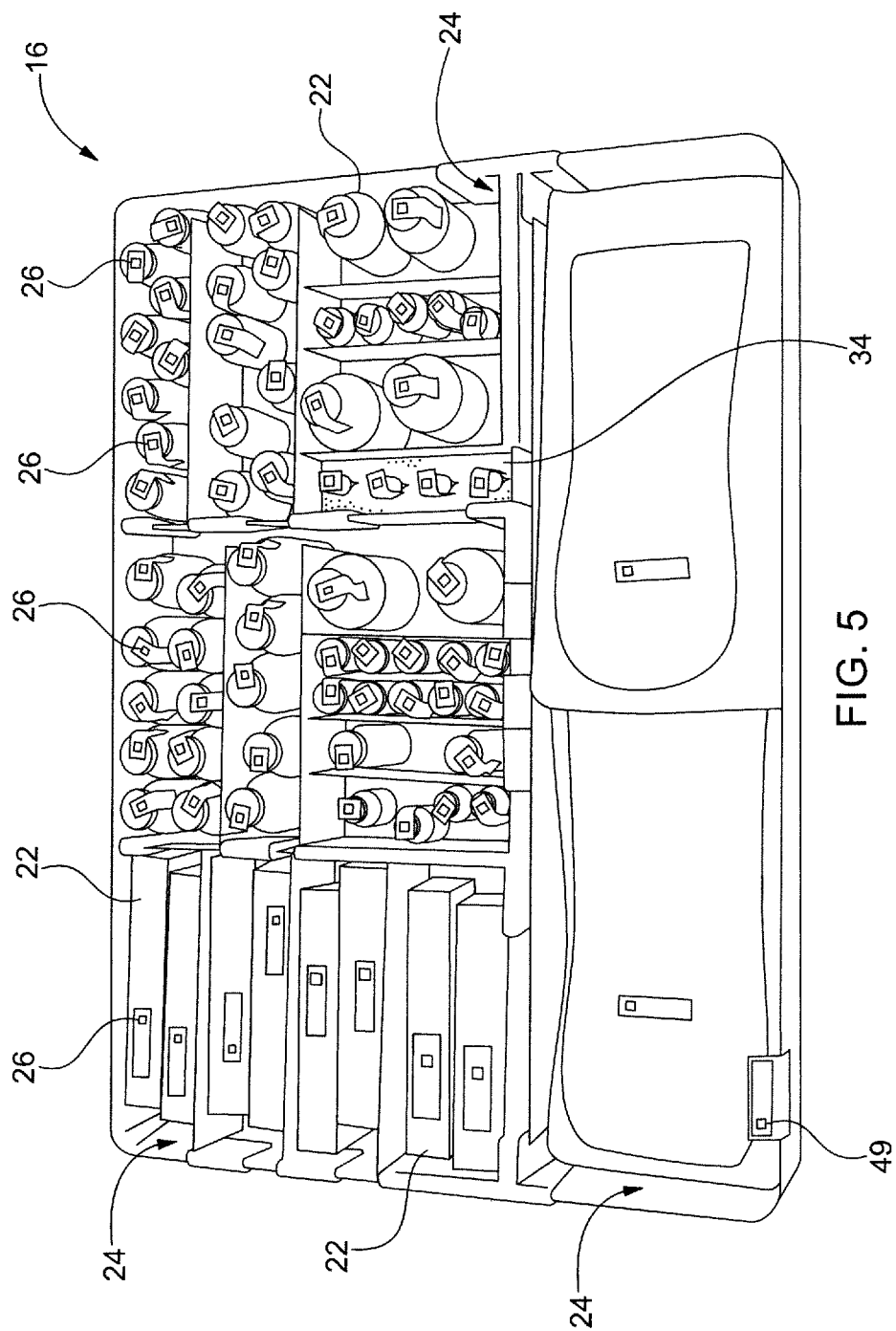
FIG. 5 is an exemplary medication tray that may be used with an inventory management system.
Figure 6B:
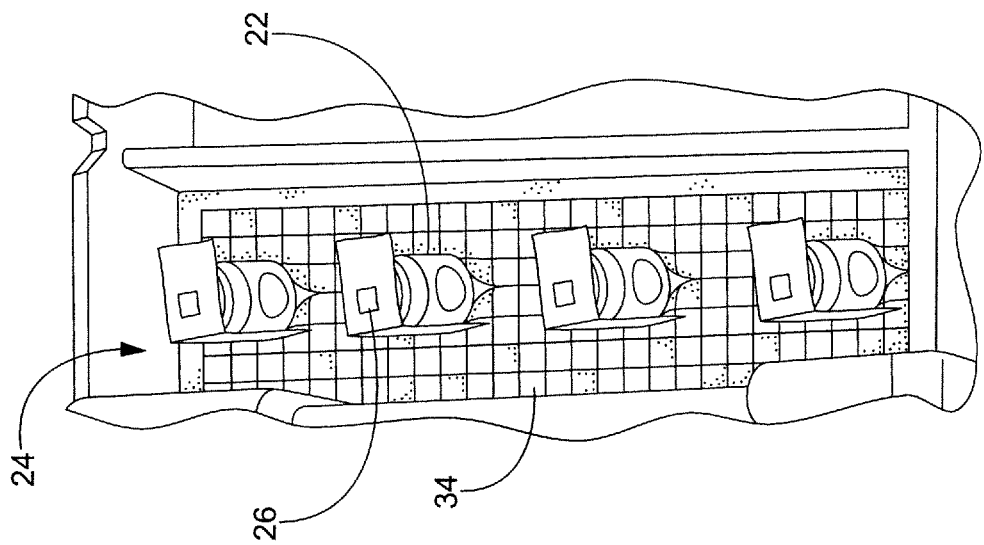
FIGS. 6A and 6B are an exemplary insert and inserts within a compartment of a medication tray, respectively, that may be used with an inventory management system.
Figure 6A:
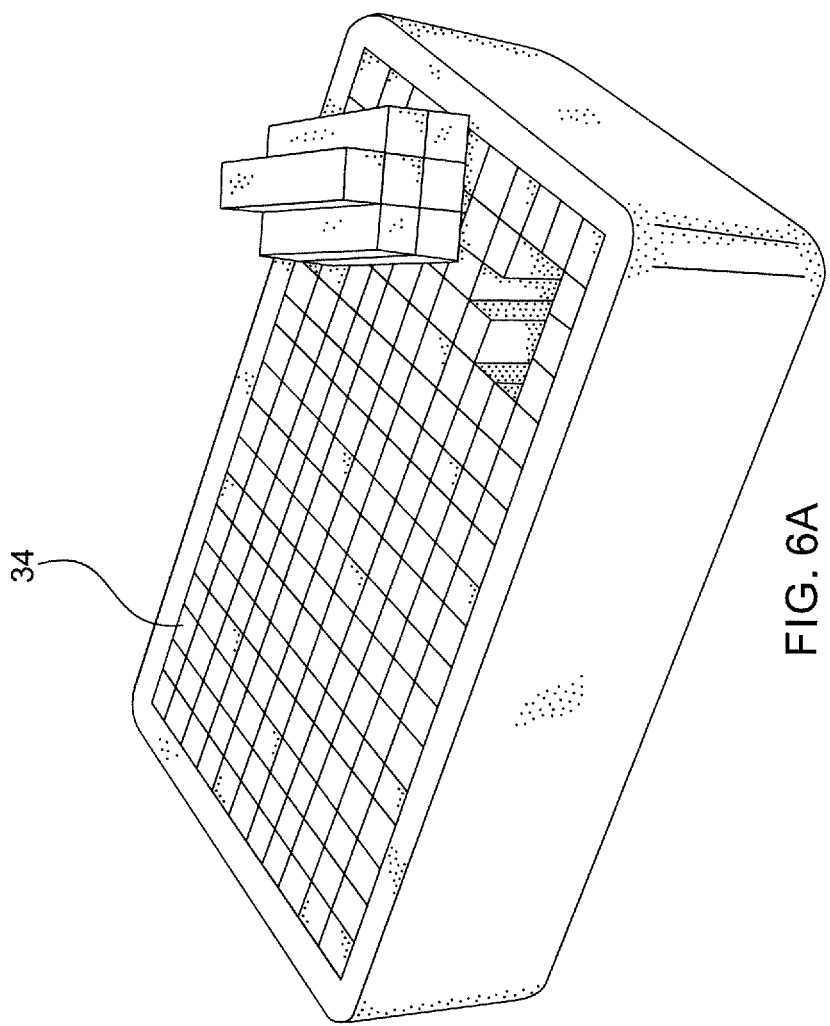

As seen in FIG. 5, a medication tray 16 can include at least one compartment 24 to receive and retain an item 22. Items 22 may exhibit various sizes and shapes, thus a medication tray 16 may have complementary sized and shaped compartments 24. A compartment 24 may be designated as a receptacle for a given item 22, and thus become a designated receptacle-compartment for that item 22. Information pertaining to a designated receptacle-compartment for an item 22 may be reduced to an item-tray recipe. An item-tray recipe for each medication tray may be generated by a user via a UI 30 to be stored in a memory of a computer device and a database of a computer system and used as a template for comparison when a medication tray 16 is subsequently scanned. Compartments 24 may also be configured to force a user to place an item 22 within a compartment in a certain orientation. For example, a compartment 24 may be shaped to only receive an item such that a marker 26 associated with that item 22 is facing in a desired direction so that light being reflected by a marker 26 is incident upon an imaging apparatus 18 (e.g., so that a marker 26 is facing upward). Thus, a shape of a compartment 24 may not only act as a visual aid to assist a user in proper placement of an item 22, but it can further help with inventory control management by ensuring that a marker 26 is facing in a direction for proper scanning by an imaging apparatus 18. This may be achieved with the use of an insert 34 having slots or other apertures enabling insertion of an item therein. For example, an insert 34 may be a foam insert 34 (see FIGS. 6A-6B) to facilitate a an interference fit of an item 22 in a compartment 24, the interference fit only being achieved if an item 22 is orientated in a certain direction. FIG. 5 shows the items 22 within the foam insert 34, where both are placed in the compartment 24. FIG. 6A shows an insert 34 that in a faun of a configurable foam block.

Markers

Figure 7B:
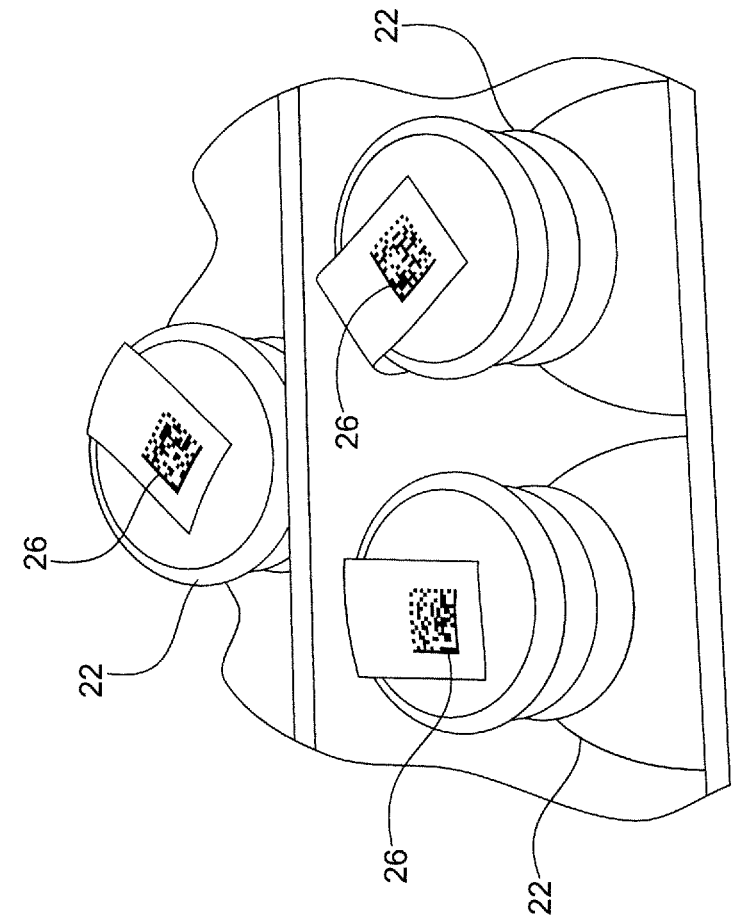
FIGS. 7A and 7B are exemplary markers and markers affixed to items, respectively, that may be used with an inventory management system.
Figure 7A:
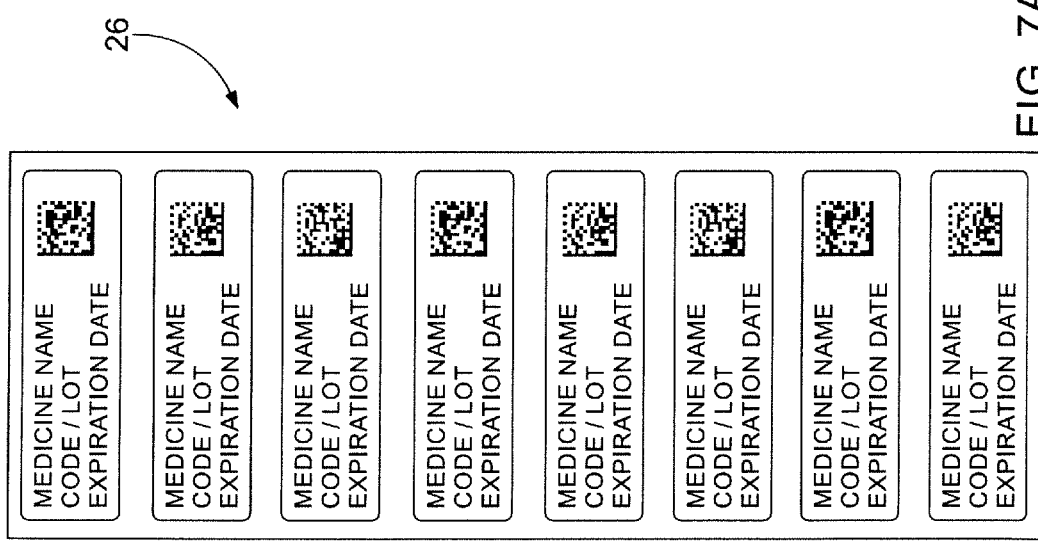

As shown in FIGS. 7A-7B, each item 22 and/or medication tray 16 may be provided with a marker 26. Each marker 26 may be a unique marker to identify and track a particular item 22 and/or medication tray 16. A marker 26 may be an optical machine-readable data symbol. For example, a marker 26 can be a barcode, and icon, an alphanumeric text, etc. In some embodiments, a marker 26 can be a 2-dimensional bar code that are also human readable. A marker 26 may be affixed to an item 22 and/or a medication tray 16 by a user during an initial inventory and setup process, or this may be done as needed during placement/replacement of items 22 and/or medication trays 16. Alternatively, a marker 26 can be affixed to an item 22 and/or a medication tray 16 by a manufacturer of the item 22 and/or medication tray 16. Furthermore, another value added agent can affix a marker 26 to an item 22 and/or medication tray 16 as part of a procurement process of the item 22 and/or medication tray 16. It is contemplated for markers 26 to be affixed to items 22 as a part of a standard item label applied by a manufacturer, including markers 26 that may be required by law or regulation to include certain identifying information (e.g., National Drug Code, lot, and/or expiration date). A marker 26 may be attached to an item 22 or medication tray 16 via adhesive applied to a label where the label is the marker. A marker 26 may be painted onto a surface of an item 22 or medication tray 16. A marker 26 may be etched into a surface of an item 22 or medication tray 16. For example a marker 26 can be generated and applied by a user during inventory, scanning, and/or replenishment via a label printer 56. (See FIG. 1).

Imaging Apparatus

An imaging apparatus 18 may include an image capturing device. In one example an image capturing device is a circuit board mounted digital camera with USB 3.0 interface. However, other image capturing devices with sufficient resolution, FOV, and digital output can be used. An imaging apparatus 18 may also include an object-presence identifier, a range detector in connection with a shelf adjustment actuator, a light exposure sensor, and/or an illumination source controller in connection with an illumination source 32 of an inventory machine 10.

Figure 8B:
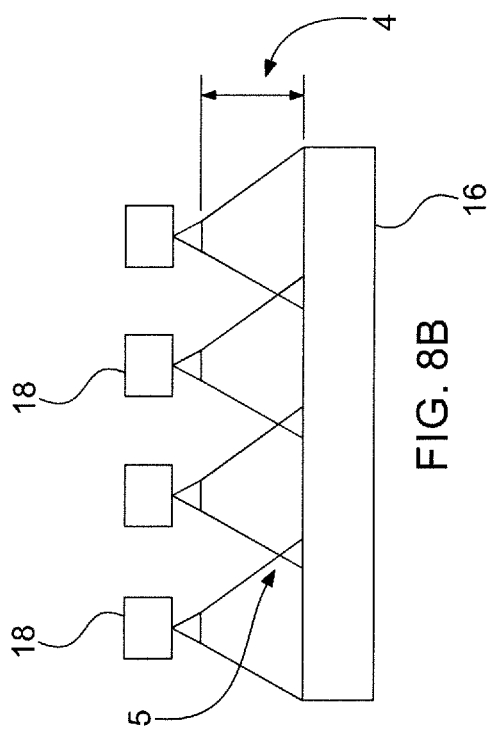
FIGS. 8A and 8B illustrate diagrams of imaging apparatus configurations, showing a single imaging apparatus and a multiple array imaging apparatus, respectively.
Figure 8A:
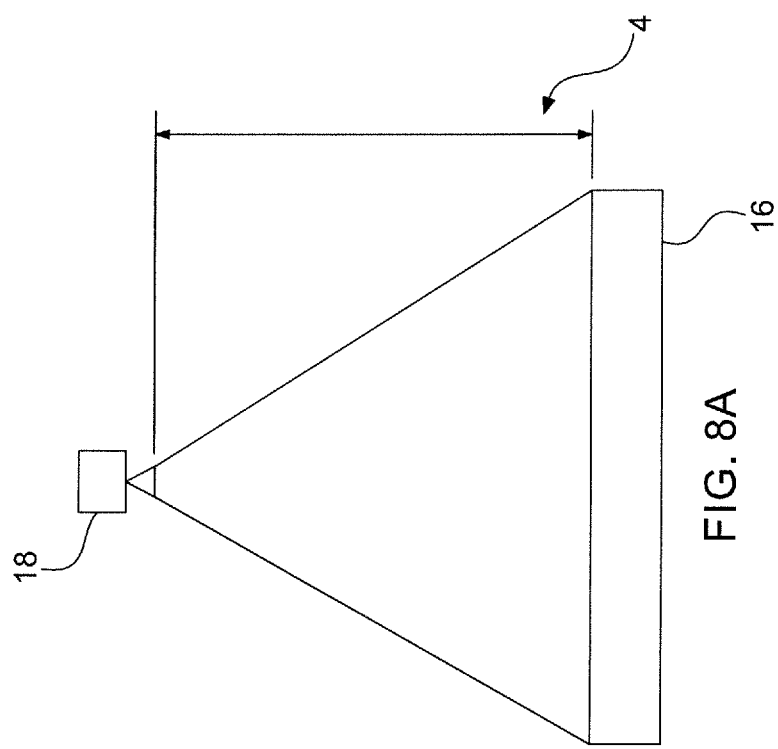

A single imaging apparatus 18, as shown in FIG. 8A, may be used to scan a medication tray and/or a compartment 24 area of a medication tray 16. Typically, a higher resolution of a captured image is desired as a scan area increased. In this regard, a large inventory machine 10 may be created to capture a workable image due to headroom 19 dimensions inside an inventory machine 10, FOV limitations, requisite standoff distance 4, etc. Standoff distance 4 can be a distance between an imager apparatus 18 and a marker 26 placed on an item 22 and/or a medication tray 16.

Alternatively, an inventory machine 10 may include a plurality of imaging apparatuses 18, as shown in FIG. 8B. The plurality of imaging apparatuses 18 can be arranged in a linear array indexed across a portion of an inventory machine 10. The plurality of imaging apparatuses 18 can be arranged in a matrix formation. With a plurality of imaging apparatuses 18, the array can be such as to create scan overlap. For example, each imaging apparatus 18 may be fixedly arranged to scan an area or sector. Arranging the plurality of imaging apparatuses 18 can be such that a scanned area or sector of a first imaging apparatus also includes a portion of a scanned area or sector of a second imaging apparatus (see FIG. 8B). This may be done to ensure adequate, if not redundant, scan coverage. This may also be done to create FOV overlap 5 so that multiple imaging apparatuses 18 can capture the same marker 26.

Generally, there is distortion at the edges of the FOV due to the angles of incidence, so this technique may be beneficial during decoding and processing. In a further embodiment, any number of the image apparatuses 18 may be actuated to perform a scan sweep, as opposed to being fixedly arranged. In this regard, an imaging apparatus 18 may be connected to the inventory machine 10 via a turret, gimbal assembly, slide-track, etc. to enable rotational and other movement of the imaging apparatus 18. Thus, a scanned area or sector can depend on a direction the imaging apparatus 18 is facing.

Generally, increasing the number of imaging apparatuses 18 results in a decrease in required resolution and may result in decreased standoff 4 requirements. Increasing the number of imaging apparatuses 18 may also reduce image distortion caused by a wider FOV (due to angles of incidence) that would otherwise be required for each image apparatus 18. For example, a single imaging apparatus 18 may have a scan sector that can capture an entire containment portion of a medication tray 16, but images captured toward the horizon of the scanned sector may be distorted due to angles of incidence. Furthermore, reducing image distortion may enable more accurate and efficient operation of a decoder apparatus 20 of an inventory management system.

In embodiments with a plurality of imaging apparatuses 18, at least one imaging apparatuses 18 may be designated as an archival imaging apparatus 36. (See FIG. 3C). An archival imaging apparatus 36 may be used to scan a sector encompassing an entire containment area of a medication tray 16, which may include every compartment 24 of a medication tray 16 and the medication tray 16 itself. Other imaging apparatuses 18 within the plurality of imaging apparatuses 18 can be used to scan individual sectors, which may include portions of the containment area of a medication tray 16. Thus, in an alternative embodiment, each portion scanned by each individual imaging apparatus 18 may be compiled to generate an image of an entire containment area of a medication tray 16. Yet, in at least one embodiment, an archival imaging apparatus 36 can be specifically designated for such a task. A benefit of using an archival imaging apparatus 36 may be to obviate an extra step of augmenting a plurality of sector images from each individual imaging apparatus 18. Another benefit may be to eliminate the angular incidence distortion at the sector image boundaries that may be generated within an augmented overall image. The archival imaging apparatus 36 may be an imaging apparatus 18 located within the matrix of imaging apparatuses 18 so as to capture an image of the entire containment area of a medication tray 16, which may include a central location. This may be a central location of the matrix and/or a central location of the medication tray 16. Alternatively, any one of the imaging apparatuses 18 of the plurality of imaging apparatuses 18 can be programmed to be an archival imaging apparatus 36 by a computer device in connection with a computer system of an inventory management system. For example, a user may designate a certain imaging apparatus 18 within the plurality of imaging apparatuses 18 to perform archival scanning and imaging via a UI 30 of a computer device.

In some embodiments, an inventory machine 10 can detect a marker 26 and decode pertinent data embodied in a marker 26 by scanning from a minimum distance to a maximum distance. For example, a scan and imaging operation may include scanning and imaging by an imaging apparatus 18 located at a minimum height achievable above a scanning sector and continue scanning and imaging as the height of the imaging apparatus 18 located above the scanning sector is increased to a maximum achievable height above a scanning sector. The minimum distance and a maximum distance can be functions of focal length of an imaging apparatus 18 and the standoff distance 4 within a medication tray receiver 14. This may be achieved by adjusting camera focus of an imaging apparatus 18 and/or adjusting a physical distance between an imaging apparatus 18 and a medication tray 16 and/or an item 22. This may be done to accommodate variances in heights of items 22 within a medication tray 16.

For example, the height of different items 22 within a given medication tray 16 may vary from approximately 0.5 inches to approximately 3.5 inches. With such a variance in height, a camera focus of an imaging apparatus 18 can be set to a midpoint, e.g., 2.0 inches, and the depth of field can include a range so as to captured acceptably sharp images for all items 22 within the 0.5 inch to 3.5 inch range. Furthermore, camera focus can be adjusted to capture multiple images at several camera focus values. Adjusting camera focus can be done electronically via a computer device, which may include inputs from a user via a UI 30. Additionally, or in the alternative, camera focus can remain fixed while a standoff distance 4 can be adjusted. Adjusting the standoff distance 4 can be achieved by moving an imaging apparatus 18 via a slide-track actuator, a telescoping extender, etc. Adjusting the standoff distance 4 can also be achieved by moving a shelf 28 upon which a medication tray 16 is resting via a shelf adjustment actuator or other means.

Figure 9:
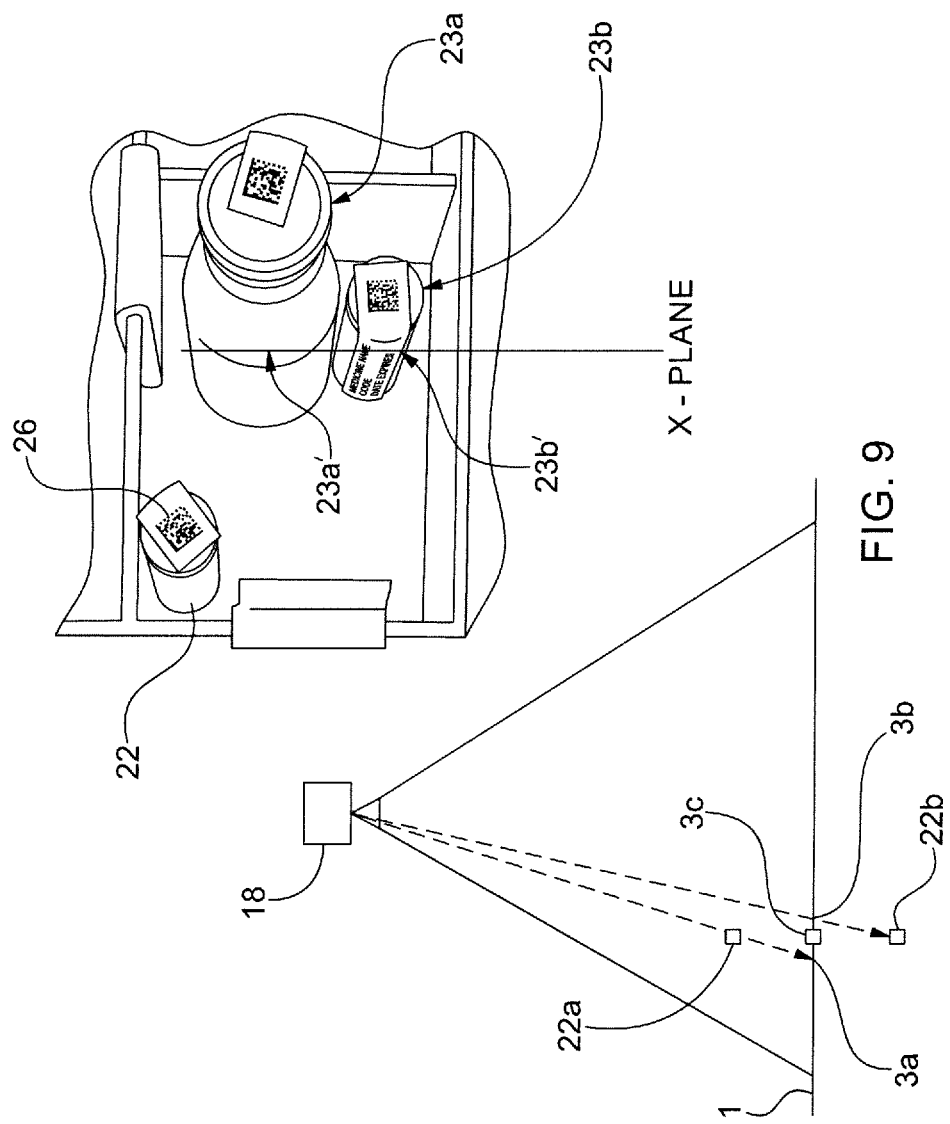
FIG. 9 illustrates a way in which the imaging apparatus can determine the exact location of the item based on marker position.

Referring to FIG. 9, when determining the exact location of an item 22 based on the marker 26 position within the image, differences in height of the item 22 can induce an apparent difference in position (see apparent position difference between item A 23a and item B 23b). This difference in apparent position may be due to parallax. For example, as shown in FIG. 9, the actual positions of item A 23a' and item B 23b' within the tray 16 are both along the x-plane, but the apparent position of the markers 26 associated with item A and item B show item A to be shifted relative to item B due to the height differential between item A and item B.

An item 22 having a height that is shorter (i.e., the top of the item 22 is below) or taller (i.e., the top of the item 22 is above) than a nominal plane 1 may appear closer or further, respectively, relative to an item 22 that has a nominal height (i.e., the top of the item is at the same level as the nominal plane). A nominal plane 1 is an arbitrary reference plane that can be used by the system to compare an item's 22 or a marker's 26 position relative to the nominal plane 1. FIG. 9 shows a "taller item" 22a and a "shorter item" 22b and the apparent image position locations 3a, 3b of each, respectively, as compared to an image position location 3c of an item 22 having a nominal height. As can be seen, a shorter item 22b may appear more to the right of image position location 3c, and a taller item 2a may appear more to the left of image position location 3c. In addition, a shorter item 22b may appear to have a smaller size as compared to the same sized item having a nominal height. Similarly, taller item 22a may appear to have a larger size as compared to the same sized item having a nominal height. Consequently, because the physical size of a marker 26 can be fixed, it can be used by a user or programmed into the system to determine the marker's 26 position relative to the nominal plane 1. For example, the actual size of the marker 26 can be compared to the apparent size of the marker 26 within the image to determine whether the marker 26 is shorter (i.e., located below the nominal plane 1) or taller (i.e., located above the nominal plane 1). A marker 26 is shorter if the apparent size is smaller than the known size, and the marker 26 is taller if the apparent size is larger than the known size.

Using this technique to estimate the height of the item 22, the location of the marker 26 can be placed more accurately in the image. For example, as noted above, the overall image also may suffer from apparent difference in position with a tall/short item 22 (especially at the outer edges of the image). Knowing the actual height of an item 22 can allow a user or the system to perform computations so that the position in the image is compensated, thereby causing it to match the marker 26 location (which may be more visually appealing than the technically more accurate x,y location in the tray 16). This may be beneficial when determining the correct receptacle-compartment for the item 22.

Manipulation and/or adjustment of camera focus and/or standoff distances 4 can facilitate capturing multiple images at differing focal lengths. If, for example, a wide range of item 22 heights is to be handled, a repository of images may be created of a same marker 26 for comparison by a computer device in order to ensure accuracy of a captured image. For instance, a computer device can be programmed to acquisition data from a memory and/or database to compare marker data with marker data of same kinds of markers 26 or the same marker 26 so as to ensure accurate identification. Performing scanning and imaging in such a manner may also facilitate obtaining sharper images at minimum item 22 heights, maximum item 22 heights, and any intermediate item 22 heights.

Adjustments to the operating parameters of an imaging apparatus 18 and/or the adjustable shelf 28 can be done to accommodate variances in item 22 height, correct for aberrations in captured images, adjust resolution, adjust sharpness, etc. For example, adjusting camera focus, shutter speed, positioning, camera sweep, etc., as well as adjusting headroom 19 and/or standoff distance 4 via adjustments in the adjustable shelf can enable tuning of focal lengths, FOVs, angles of incidence, etc.

In some embodiments, focal lengths at which the images can be taken may be pre-determined and input as operating parameters in a computer device. One of the factors for setting the focal lengths may be expected attributes of items 22 within a given imaging FOV. Auto-focusing techniques may be used as the focal lengths are indexed and the scanning is performed.

Decoder

Figure 10:
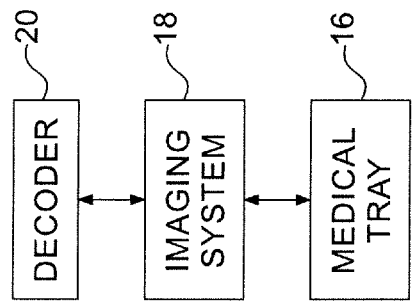
FIG. 10 illustrates a block diagram of an inventory management system with a decoder in connection with an imaging apparatus to image and scan a medication tray.

A decoder 20, shown in FIG. 10, may include an optical character recognition ("OCR") device to detect markers 26. A decoder 20 may also be used to decode pertinent data embodied in a marker 26. OCR may be used as an alternative to barcodes, and could be used to read the information directly from an item label (e.g., NDC, lot number, expiration date, etc.). For example, it is contemplated for manufacturers to directly label items 22 with a Data Matrix barcode containing this information. Various image processing techniques can be used to locate barcodes from a background of a label (e.g., the size and shape expected), enhance an image for decoding, and decode with available barcode decoding libraries.

In addition, various object recognition techniques may be used to enhance the performance of a decoder 20 in locating and decoding markers 26. For example, a size, a shape, a color, a pattern, etc. of an item 22 can be used to detect if an item 22 is within its designated receptacle-compartment, if an item 22 is missing, if an item 22 is misplaced, etc. These techniques may also be used to determine an orientation of an item 22 for purposes of locating a marker 26 or more accurately determining a location of a marker 26. These techniques may also be used to augment detection of markers 26, if markers 26 are unreadable by an imaging apparatus 18 and/or a decoder 20. Thus, items 22 may still be identified and tracked where their associated markers 26 have been damaged, missing, and/or rotated out of view. For example, aberrations in sharpness can be detected and may be generally corrected for by adjusting focal length. Yet, the physical size of a barcode and/or Data Matrix size can be known before use with an inventory management system. Thus, an inventory management system can be used to determine if a marker 26 is attached to an item 22 or not attached to an item 22 by detecting a very poor sharpness that a focus adjustment cannot correct. In other words, an inventory management system can determine if a barcode is present/not present, even if it cannot be decoded (e.g., because focus is so bad, generating too many errors). Furthermore, a Data Matrix format has multiple elements that are fixed to more easily locate for items 22. For example, the multiple recognizable elements that are fixed can be used to compensate for an item 22 that may be rotated and still identify the item 22. Thus, a Data Matrix format can facilitate compensating for rotation and x/y scaling effects when reading barcodes.

Data from a decoder 20 can be used by a computer device to adjust operating parameters of an inventory management system. For example, decoder data can be used to detect that an adjustment in focal length of an imaging apparatus 18 is required. The decoder data can then be used to make the adjustment to improve a probability of successfully detecting and decoding a marker 26. A computer device may perform this adjustment automatically and/or generate a textual display on a screen display of a UI 30 of a computer device to inform a user that a manual inspection of a component of an inventory system may be required and/or that an adjustment in the operating parameters may be required. For example, a computer device may inform a user that a manual inspection of a medication tray 16 should be performed, that standoff distance 4 should be adjusted, that the frequency of light emanated from an illumination source 32 should be adjusted, etc.

Inventory Management User Interface

Figure 11A:
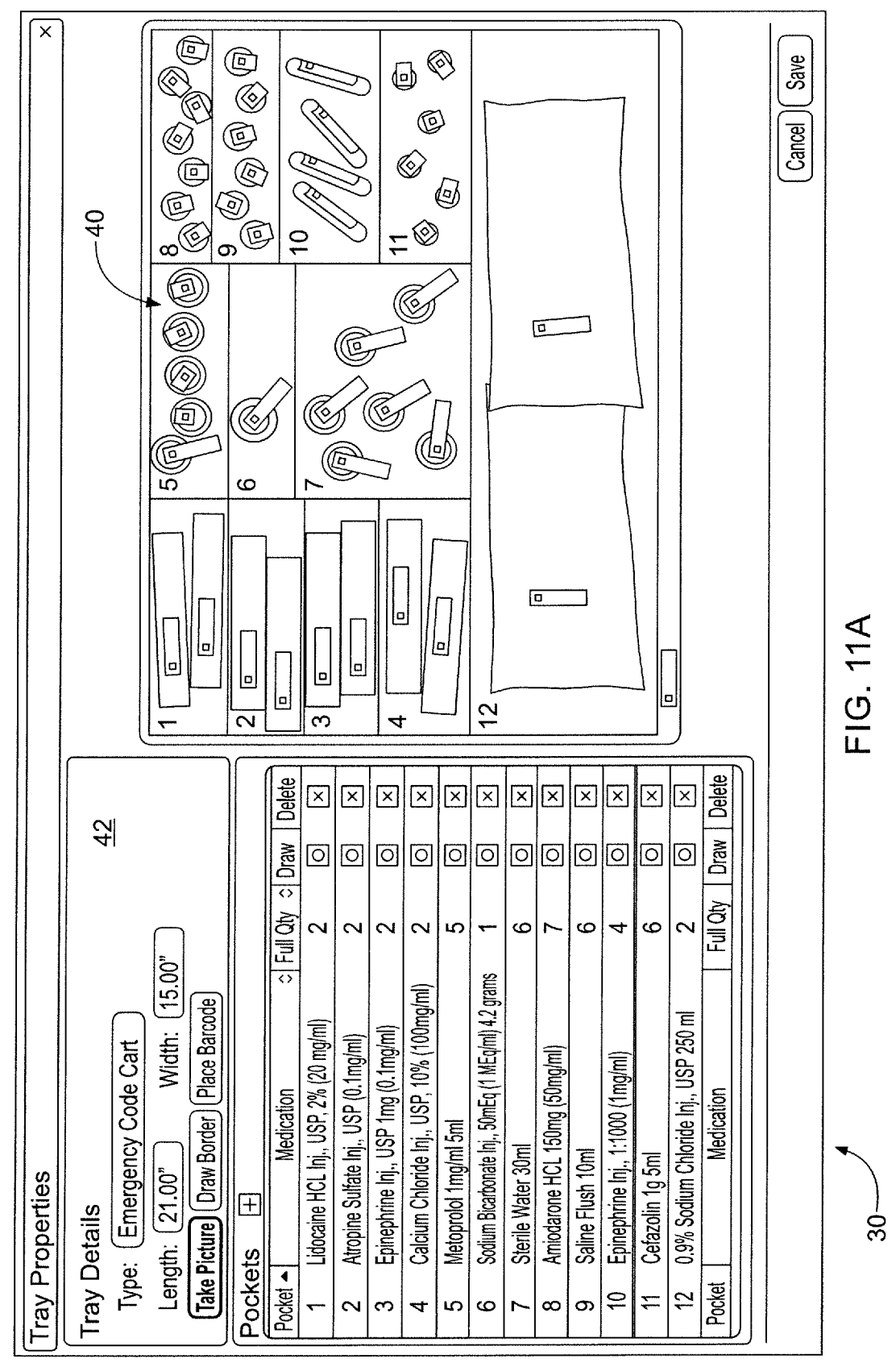
Figure 11B:
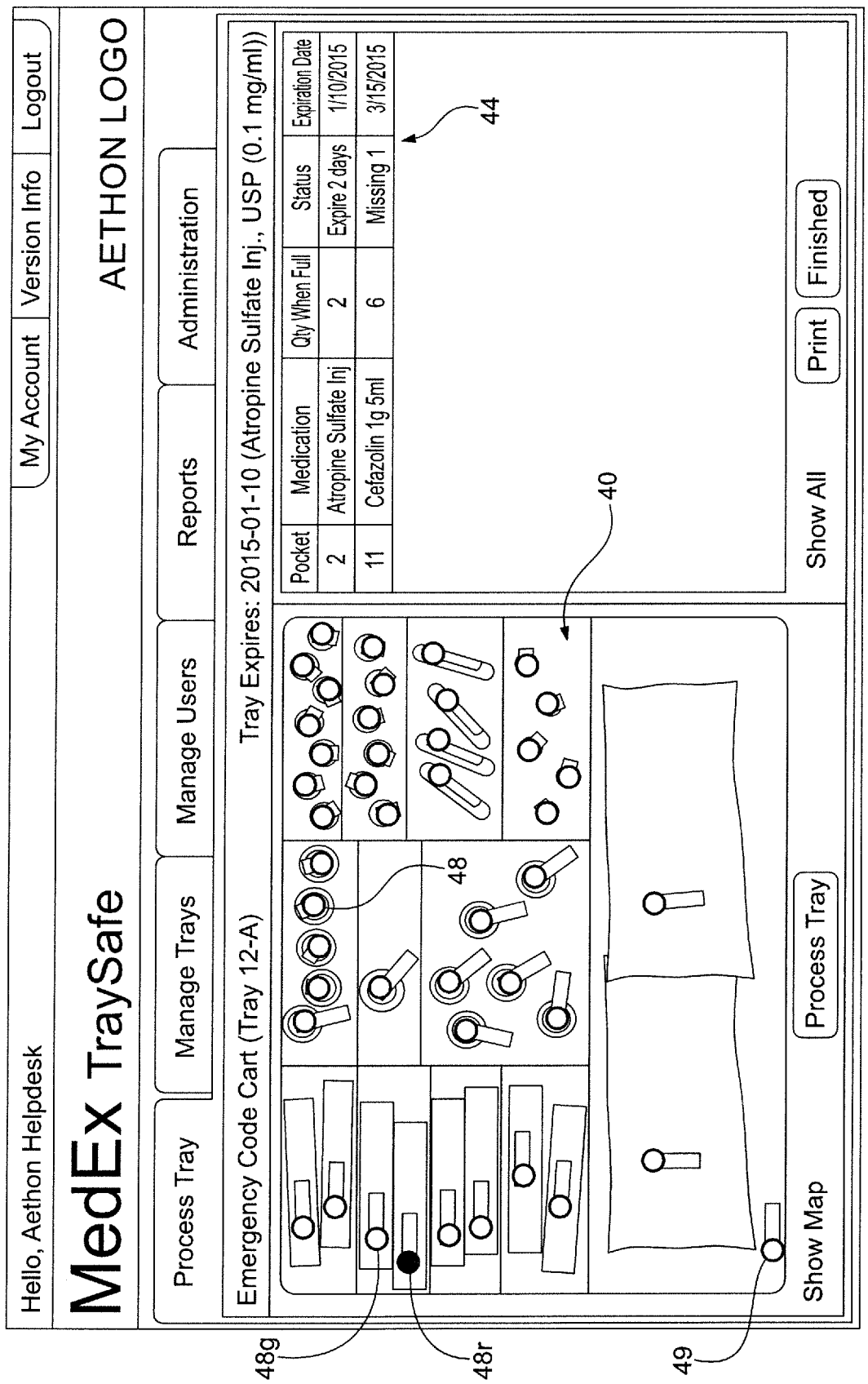

An inventory management system may be configured such that upon scanning and decoding a marker 26 of an item 22 and/or a medication tray 16, pertinent data can be transmitted to a computer device to be acquisitioned and processed by a processor in accordance with commands inputted via a UI 30 and/or in accordance with algorithms of a processor. For example, an UI 30 may be displayed on a computer device, and may be programmed to generate various modules, panels, and screen displays. Control of an inventory machine 10 and/or other components of an inventory management system, as well as generation of reports 38 related to inventory management may be accessible and/or formatted with use of GUIs and/or actuable indicia displayed on any of the UIs 30. For instance, a tray display screen 40 may be programmed to show an image of a medication tray overlaid with indictors superimposed on items within a medication tray 16. (See FIGS. 11A-11B). A tray screen display 40 may also be programmed to display additional identifying, status, and statistical data about items 22 and/or medication trays 16, as well as pertinent data obtained from markers 26 associated with an item 22 and/or medication tray 16. For instance, a summary tray screen 42 may be displayed adjacent a tray screen display 40. (See FIG. 11A). A summary tray screen 42 and/or an item usage screen display 44 (see FIG. 11B) may be programmed to display other pertinent data, which may be obtained from pharmacies, manufacturers, and other entities via a computer network. Other pertinent data may include recall data disseminated by manufacturers, insurers, regulators, etc., quantity when full information, status information, expiration date information, etc.

Figure 11C:
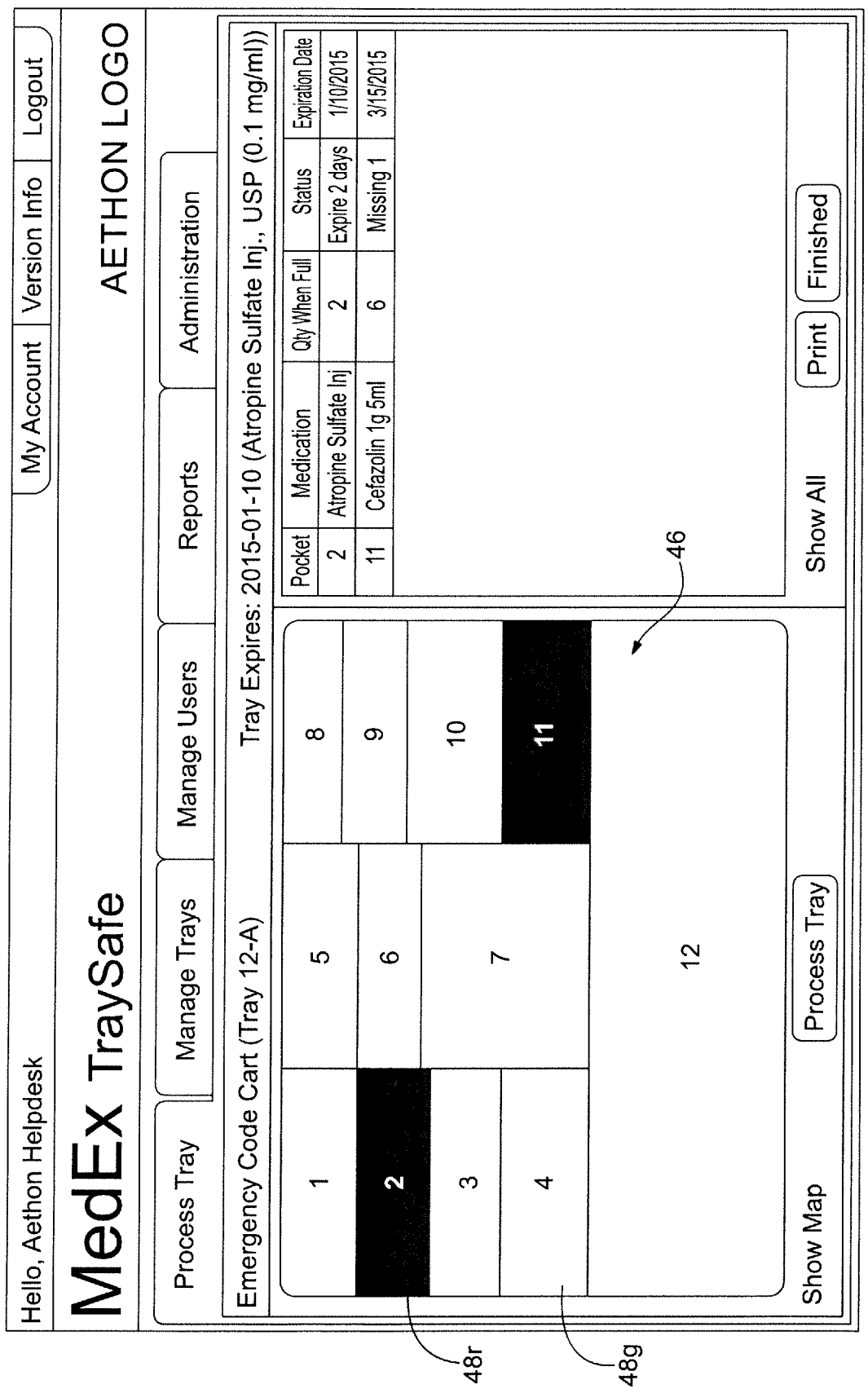
Figure 11D:
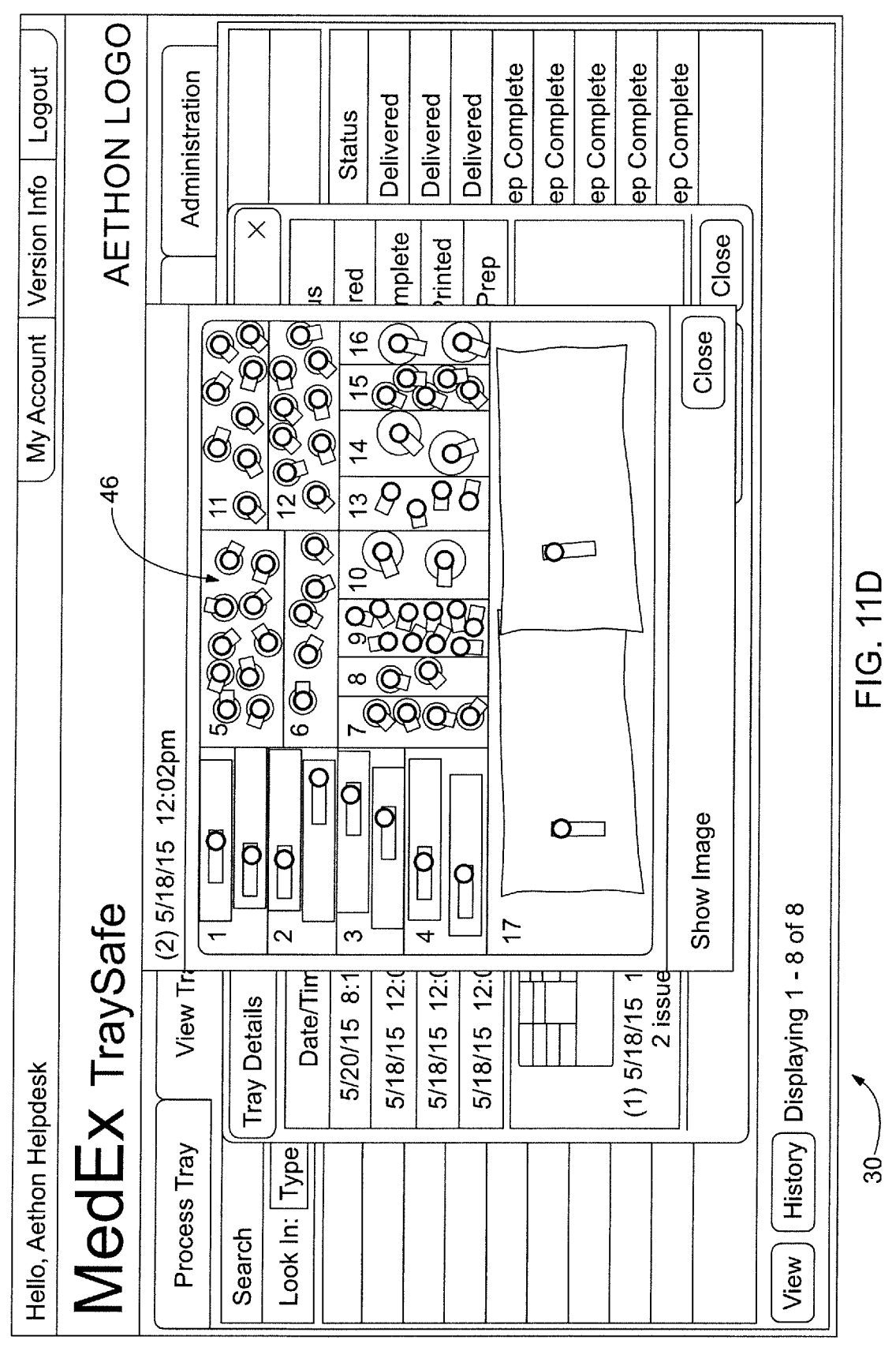

An item-recipe compare screen display 46 may include indicators 48 informing a user which items 22 are in their designated receptacle-compartment and which items are not. (See FIG. 11C-11D). This may include a color coded chart with cells representing designated receptacle-compartments. Proxy values for each item 22 may be displayed in the cells to inform users which designated receptacle-compartment is missing an item 22 and/or has a correct/incorrect item 22 placed within it. Furthermore, a computer device can be programmed to generate a color coded indicator 48 superimposed on an item 22 and/or a compartment 24 of a medication tray 16, the color of the color coded indicator 48 representing a status of the item 22. (See FIG. 11B). For example, a red indicator 48*r* superimposed on an item 22 may represent that an item 22 is not in its designated receptacle-compartment, whereas a green indicator 48*g* superimposed on an item 22 may represent that an item 22 is in its designated receptacle-compartment. A tray identifier indicator 49 is also provided to identify the particular tray 16.

Figure 11E:
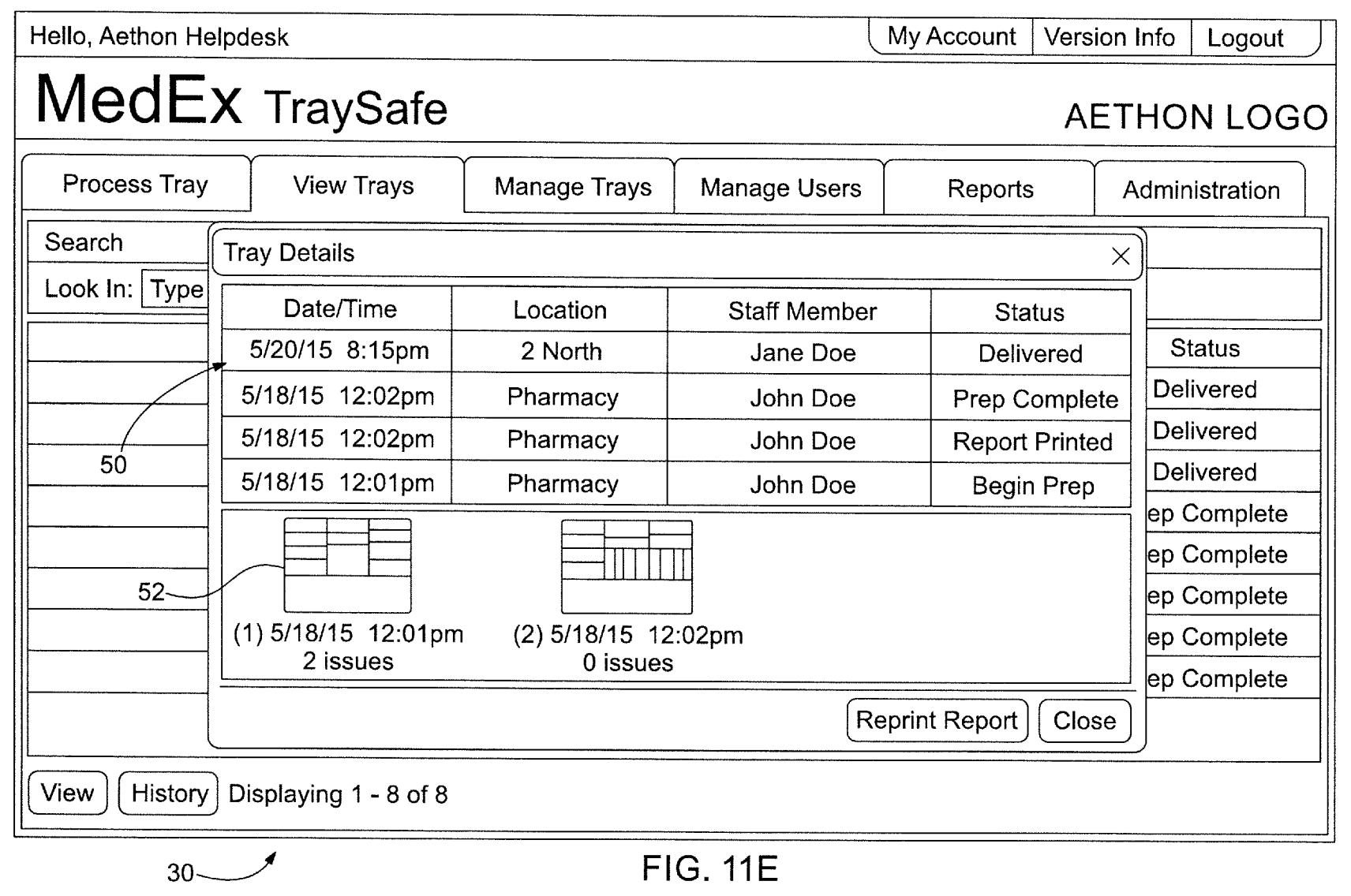

Hand-held readers may be used to track items 22 and/or medication trays 16. For example, hand-held readers can be used to track items 22 and/or medication trays 16 as an item 22 and/or medication tray 16 is transported through the hospital. Data from the hand-held reader may be used to generate a medication tracking screen display 50. (See FIG. 11E). A medication tracking screen display 50 may be programmed to display data related to dates/times when an item 22 and/or medication tray 16 was at a particular location within a hospital and/or used for disseminating medication to a patient. This may also include a staff member tasked to deliver the item 22 and/or medication tray 16 to the location or disseminate the medication to the patient, and a status of the delivery. Each item 22 and/or medication tray 16 may be represented by an icon 52 (e.g., a picture of the item 22 and/or medication tray 16 that may have been taken by an archival imaging apparatus 36), and displayed on a portion of a medication tracking screen display 50. Statistical data (date/time, number of issues, etc.) about an item 22 and/or medication tray 16 may also be displayed adjacent the icon 52.

Reports 38 may be generated at the discretion of a user of an inventory management system and/or automatically by a computer device of an inventory management system. A report 38 may be in electronic format and displayed via a UI 30, from which it may be printed, saved in the memory of a computer device, and/or transmitted to another computer device via a computer system. Reports 38 can be in tabular form (see FIG. 12); however, report 38 formats can be pre-set and/or modifiable. For example, a report 38 can include any of the information displayed on any of the display screens 40, 42, 44, 46, 50, and user may modify and/or create report 38 formats to display the type of information most beneficial for a particular application. The report 38 includes at least the location of each medication by compartment, the name of the medication, the full quantity that should be in the tray if full, the replaced quantity, and the expiration date.

Images scanned, generated screen displays 40, 42, 44, 46, 50, and/or generated reports 38 for each item 22 and/or medication tray 16 may be collected and stored in separate inventory management system memory and/or database banks to be accessed at the discretion of the user and/or accessed automatically by a computer device of a computer system for historical, audit, and/or other inventory management purposes.

Inventory Management Method

A marker 26 can be generated for each item 22 and/or medication tray 16, where each marker 26 can be encoded with pertinent data. A marker 26 can then be further associated with an item 22 and/or medication tray 16. This may include physically attaching a marker 26 to an item 22 and/or medication tray 16. Further associating a marker 26 with an item 22 and/or medication tray 16 can be performed during manufacture of, procurement of, and/or initial inventory of an item 22 and/or medication tray 16. Pertinent data can include lot codes, which may be provided by a manufacturer to denote a batch of a product used to generate an item 22. Lot codes can be used for auditing and other purposes (e.g., product recalls). A compartment 24 of a medication tray 16 can then be identified as a designated receptacle-compartment for an item 22. At least one item-tray recipe can be generated corresponding to kind, count, and location of all items 22 in a medication tray 16 in accordance with assigned designated receptacle-compartments. For example, an item-tray recipe can be a set of designated receptacle-compartments and associated items 22 for a given application.

It is contemplated that sets of item-tray recipes may be used as standards for user of an inventory management system to use. Further embodiments can include modifying item-tray recipes for a given application, a given facility, and/or a given user. The item-tray recipes can be created and/or modified, which may be done using software tools, which may then be maintained by a memory of a computer device and/or a database of a computer system. Software tools used to generate item-tray recipes can range from simple software-related spreadsheets to UI-based and GUI-based systems. UI-based and/or GUI-based systems may be better suited for determining designated receptacle-compartments, assigning items 22 with designated receptacle-compartments, and/or generating schematic representations of a medication tray 16. In some embodiments, a schematic representation of a medication tray 16 can be used with an item-tray recipe to define designated receptacle-compartments. Alternatively, co-ordinates can be associated with individual items 22 and be specified directly in a definition of an item-tray recipe. Similarly, a recipe may be generated for each medication tray 16, where the medication-tray recipe may be associated with an item-tray recipe. Data pertaining to the item-tray recipe and/or the medication-tray recipes can then be stored in a memory of a computer device and/or a database of a computer system.

Items 22 and/or medication trays 16 received at a hospital and/or a location within a hospital can be inventoried. If items 22 are received by a hospital outside of the compartments 24 of a medication tray 16, items 22 can be placed in the medication trays 16 in accordance with an item-tray recipe and/or a medication-tray recipe. For example, items 22 may be placed in designated receptacle-compartments in accordance with an item-tray recipe and/or a medication-tray recipe that has been accessed via a computer device from a memory of a computer device and/or a database of a computer system. Alternatively, items 22 may be placed in designated receptacle-compartments in accordance with an item-tray recipe and/or a medication-tray recipe that has been generated by users of the received items 22.

When placed in a medication tray 16, items 22 may be placed within foam inserts 34 to ensure that a marker 26 associated with an item 22 is in a direction for proper scanning. A medication tray 16 can then be scanned as an initial inventory scan via an inventory machine 10 and/or a hand-held reader. This may cause a computer device to generate a UI 30 displaying a tray display screen 40 or other screen display 42, 44, 46, 50. A user may review a display screen 40, 42, 44, 46, 50 to determine if any items 22 are misplaced and/or un-scannable. Alternatively, or in addition, a computer device can be programmed to display a message informing a user that all items are in a proper place, that an item 22 is out of place, that an adjustment in an operating parameter should be performed, that the computer device is going to make an adjustment to an operating parameter automatically, etc. If there is an inconsistency, an adjustment is requested, or some other indicator causing concern (e.g., expiration date lapsed, recall, etc.), etc., a subsequent scan can be requested after prompting a user to take corrective action. If after a subsequent scan, or if upon an initial inventory scan, all of the items are properly identified, properly placed within designated receptacle-compartments, no information causing concern is detected, and no adjustments are requested, then a concluding scan may be performed. A concluding scan can be the most recent scan that identified no inconsistencies, corrective actions to be taken, and/or no information causing concern. Alternatively, a concluding scan can be an additional subsequent scan requested by the inventory management system. A concluding scan may be used to generate an inventory record and/or a comparison template for a next inventory scan of the medication tray 16. A concluding scan can also include an image from an archival imaging apparatus 36 to be used as a comparison template.

After an initial inventory scan, a medication tray 16 can be placed in a storage area and/or marshaling area for use by the hospital. Pertinent data obtained during an initial inventory scan can be stored in a memory of a computer device and/or database of a computer system to be tracked for auditing and/or quality control purposes. Pertinent data can be data inputted by a user, data sent by a manufacture/retailer of the item 22, and/or data received by a computer device via a computer system from another party (e.g., insurer, doctor, pharmacist, government regulator, etc.). For example, if an expiration date of an item 22 is approaching, a computer device may be programmed to generate a communication to a user via a UI 30 to inform a user that the item 22 should be used soon and/or replaced. In addition, a computer device of a computer system can be programmed to receive communications from other computer devices of a computer system including pertinent data for an item 22. For example, a manufacturer, insurer, government regulator, may communicate a recall for an item 22. Upon receiving such pertinent information, the computer device can update the pertinent data and generate a communication to a user via a UI 30 to replace the item 22. A computer device can be programmed to receive pertinent data periodically, continuously, at the discretion of a user, whether a scan is being performed or not, etc. Upon receiving new or additional pertinent data, a computer device can be programmed to request an additional scan to update the pertinent data of a marker 26. This may include printing a new marker 26 to be placed on the item 22 and/or medication tray 16. This may also include saving the pertinent data in a memory of a computer device and/or a database of a computer system to be accesses regardless of a marker 26 being scanned.

A medication tray 16, after undergoing an initial inventory scanning, can be used to delivery and/or disseminate medications throughout a hospital. Staff members tasked with transporting medication trays 16 and disseminating medications can be forced to place items 22 in their designated receptacle-compartments due to the inserts 34. Staff members tasked with transporting medication trays 16 and patients and/or departments that are intended recipients of the items 22 can be associated with a medication tray 16 and/or items 22 within the medication tray 16 so that the movement of the medication tray 16 and/or the items 22 can be tracked with reference to the staff member, patient, and/or department.

The inventory management system can be programmed to automatically track items 22 and medication trays 16 and determine replacement, recalls, expirations, uses, etc. of medications based on pertinent data and scanned information. For example, the inventory management system can be programmed such that each medication tray 16 must be scanned before being transported from its storage area, otherwise issue an alert. The inventory management system can be further programmed to request periodic scanning of a medical tray 16, otherwise issue an alert. The inventory management system can be further programmed to request a scanning after each scheduled transportation and/or dissemination of an item 22, whether the medication tray 16 was actually transported and/or whether an item 22 was actually disseminated, otherwise issue an alert. The inventory management system can be further programmed to request a scanning if a medication tray 16 has been transported and not returned to its storage area after a certain amount of time has elapsed. Other requested scanning schemes and schedules can be used. Thus, the inventory management system can track medication trays 16 and/or items 22 whether they are inside an inventory machine 10 or not.

Figure 13:
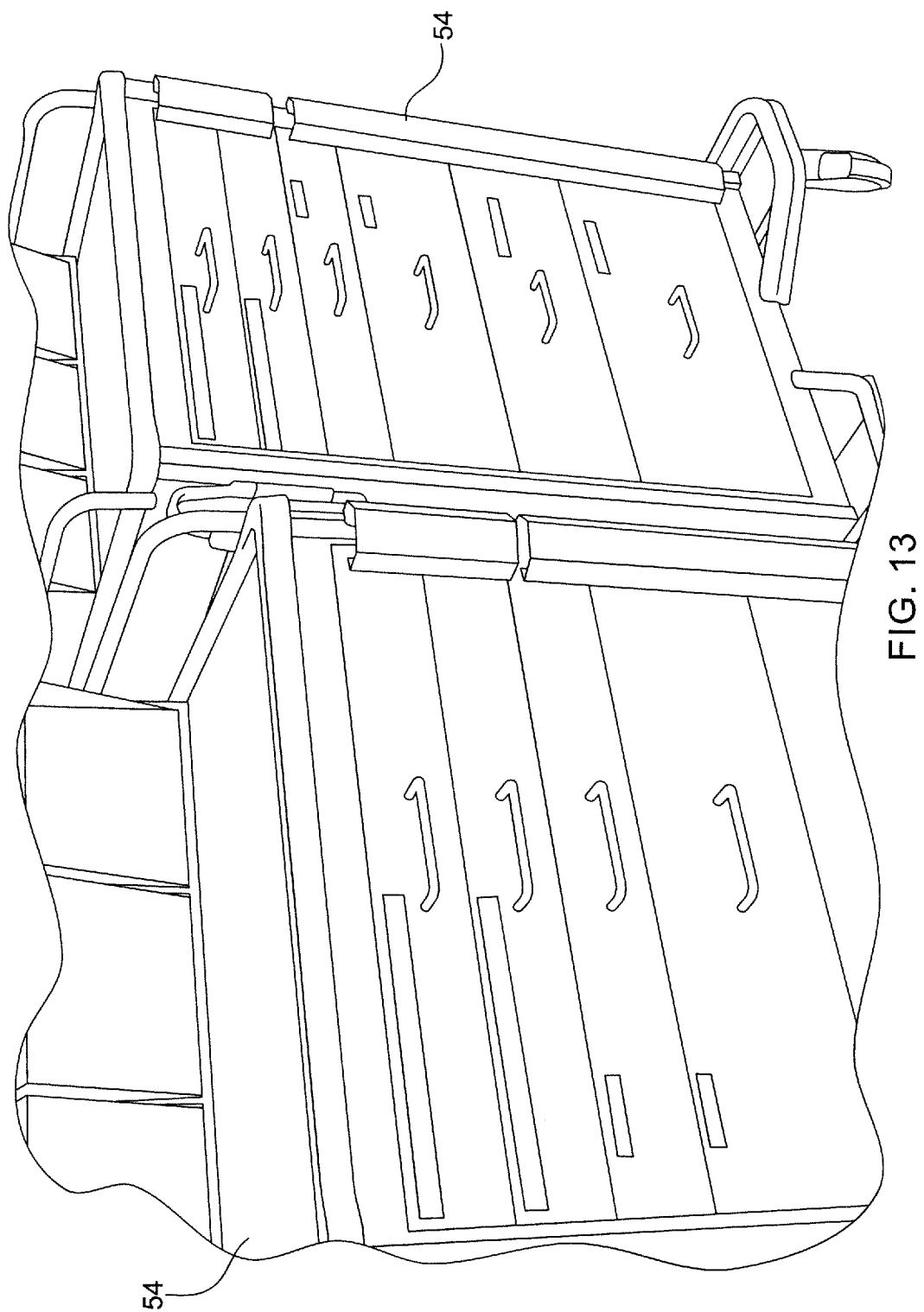
FIG. 13 is a crash cart that may be used with an inventory management system; and, FIG. 14 is an exemplary computer system that may be used with an inventory management system.

Reports 38 and/or notifications may be automatically generated to inform a user that an item 22 and/or a medication tray 16 should be scanned, removed, restocked, and/or replaced. Other reports 38 and/or notifications may be automatically generated to inform a user of a status of an item 22 and/or medication tray 16. For example, the inventory management system may generate a report 38 and/or notification via a computer device for a user to retrieve a medication tray 16 from a location within the facility for scanning and/or replenishment. An inventory management system can maintain the current status and location of all medication trays 16, including medication trays 16 located outside its storage area (e.g., medication trays 16 located within crash carts—see FIG. 13). Thus, the inventory management system may inform a user to retrieve a medication tray 16 from a particular crash cart 54 to perform a routine scan and/or perform a replenishment of certain items 22.

A subsequent scan can be achieved by inserting a medical tray 16 into an inventory machine 10 and/or by scanning performed by a hand-held reader. During a subsequent scan, just as with an initial inventory scan, item-tray recipes and medication-tray recipes can be used to compare actual item 22 locations to their associated designated receptacle-compartments. During a subsequent scan, just as with an initial inventory scan, a computer device can be caused to display a screen display 40, 42, 44, 46, 50 with indicators informing a user which items 22 are in their designated receptacle-compartment and which items 22 are not, as well as other status and statistic information about an item 22 and/or a medication tray 16. Each subsequent scan may also cause a computer device to generate a UI 30 to enable a user to update an item-tray recipe and/or a medication tray recipe. Each subsequent scan can also cause a computer device to display a message informing a user that all items 22 are in a proper place, that an item is out of place, that an adjustment in an operating parameter should be performed, that the computer device is going to make an adjustment to an operating parameter automatically, etc.

Each scan session can cause a computer device to generate screen displays 40, 42, 44, 46, 50 via a UI 30, as well as a report 38, all of which may provide statistical and status information about an item 22 and/or a medication tray 16. A report 38 can include an exception list, providing a list of items 22 that are missing, items 22 that are in the incorrect location, and/or items 22 not meeting criteria of lot code, expiration date, soon-to-expire date, etc. After each subsequent scan, and based upon reports 38 generated, replenishment may occur to remove, restock, and/or replace items 22 within a medication tray 16. Additional data comparisons, such as comparing acceptable/allowable conditions with expiration date, soon-to-expire date, and/or recall information may further enable users conduct inventory management by ensuring such items 22 are in compliance. Each replenishment may result in a requested subsequent scan, which may cause a computer device to generate a UI 30 to enable a user to update an item-tray recipe and/or a medication tray recipe.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A medication inventory management system comprising:
    a medication tray comprising a plurality of partitions defining a plurality of compartments, the medication tray having a tray identifier associated therewith, each compartment for storing a respective different medication having a medication identifier associated therewith and each compartment having an open unlidded upper end for access to the respective medication by medical personnel;
    at least one imaging apparatus configured to view the respective medication identifiers through the open unlidded upper ends of the plurality of compartments; and
    a processor and an associated memory configured to
        cooperate with said at least one imaging apparatus to determine the tray identifier and medication identifiers of the medication tray,
        maintain in the memory a desired respective medication within each compartment based upon the tray identifier,
        determine the respective medication within each of the plurality of compartments based upon the medication identifiers, and
        determine a discrepancy from among a plurality of different discrepancies between the determined respective medication within each compartment and the desired respective medication within each compartment, and when so generate a display notification comprising an image of the medication tray with a visual indicator corresponding to each compartment determined to have the discrepancy overlaid thereon the image of the medication tray, and a textual indicator indicating the corresponding discrepancy from among the plurality of different discrepancies with the associated compartment for each compartment determined to have the discrepancy, the plurality of different discrepancies comprising a medication expiration discrepancy and an incorrect medication discrepancy; and
    a display coupled to the processor for displaying the display notification.

2. The system of claim 1 further comprising a medication tray housing to receive said medication tray.

3. The system of claim 1 wherein the display notification comprises a further visual indicator corresponding to each compartment determined to not have a discrepancy; and wherein the further visual indicator and visual indicator have different visual characteristics.

4. The system of claim 1 wherein the visual indicator comprises a colored indicator.

5. The system of claim 1 wherein the plurality of different discrepancies comprises a recalled medication discrepancy.

6. The system of claim 1 further comprising an illumination source spaced above said medication tray.

7. The system of claim 1 wherein the tray identifier comprises a tray barcode.

8. The system of claim 1 wherein the at least one medication identifier comprises a medication barcode.

9. The system of claim 1 wherein the medication identifiers comprise alphanumeric text; and wherein said processor is configured to perform an optical character recognition of the alphanumeric text to determine the respective medication within each of the plurality of compartments.

10. The system of claim 1 further comprising:
    a medication tray housing to receive said medication tray;
    a medication shelf actuator carried by said medication tray housing; and
    a range detector carried by said medication tray housing;
    said processor being configured to determine a focal distance between said medication tray and said at least one imaging apparatus based upon said range detector and selectively operate said shelf actuator based upon the focal distance.

11. The system of claim 1 wherein said at least one imaging apparatus comprises a plurality of imaging apparatuses.

12. A medication inventory device for a medication inventory management system comprising a medication tray comprising a plurality of partitions defining a plurality of compartments, the medication tray having a tray identifier associated therewith, each compartment for storing a respective medication having a medication identifier associated therewith and each compartment having an open upper unlidded end for access to the respective medication by medical personnel, the medication inventory device comprising:
    at least one imaging apparatus configured to view the respective medication identifiers through the open unlidded upper ends of the plurality of compartments;
    a processor and associated memory configured to
        cooperate with said at least one imaging apparatus to determine the tray identifier and medication identifiers of the medication tray,
        maintain in the memory a desired respective medication within each compartment based upon the tray identifier, determine the respective medication within each of the plurality of compartments based upon the medication identifiers, and determine a discrepancy from among a plurality of different discrepancies between the determined respective medication within each compartment and the desired respective medication within each compartment, and when so generate a display notification comprising an image of the medication tray with a visual indicator corresponding to each compartment determined to have the discrepancy overlaid thereon the image of the medication tray, and a textual indicator indicating the corresponding discrepancy from among the plurality of different discrepancies with the associated compartment for each compartment determined to have the discrepancy, the plurality of different discrepancies comprising a medication expiration discrepancy and an incorrect medication discrepancy; and a display coupled to the processor for displaying the display notification.

13. The medication inventory device of claim 12 wherein the display notification comprises a further visual indicator corresponding to each compartment determined to not have a discrepancy; and wherein the further visual indicator and visual indicator have different visual characteristics.

14. The medication inventory device of claim 12 wherein the visual indicator comprises a colored indicator.

15. The medication inventory device of claim 12 wherein the plurality of different medication discrepancies comprises a recalled medication discrepancy.

16. A method of managing medication inventory in a medication inventory management system comprising a medication tray comprising a plurality of partitions defining a plurality of compartments, the medication tray having a tray identifier associated therewith, each compartment for storing a respective medication having a medication identifier associated therewith and each compartment having an open unlidded upper end for access to the respective medication by medical personnel, the method comprising:

operating at least one imaging apparatus configured to view the respective medication identifiers through the open unlidded upper ends of the plurality of compartments; and using a processor and associated memory to
cooperate with the at least one imaging apparatus to determine the tray identifier and medication identifiers of the medication tray,
maintain in the memory a desired respective medication within each compartment based upon the tray identifier,
determine the respective medication within each of the plurality of compartments based upon the medication identifiers,
determine a discrepancy from among a plurality of different discrepancies between the determined respective medication within each compartment and the desired respective medication within each compartment, and when so generate a display notification comprising an image of the medication tray with a visual indicator corresponding to each compartment determined to have the discrepancy overlaid thereon the image of the medication tray, and a textual indicator indicating the corresponding discrepancy from among the plurality of different discrepancies with the associated compartment for each compartment determined to have the discrepancy, the plurality of different discrepancies comprising a medication expiration discrepancy and an incorrect medication discrepancy, and cooperating with a display coupled to the processor to display the display notification.

17. The method of claim 16 wherein the display notification comprises a further visual indicator corresponding to each compartment determined to not have a discrepancy; and wherein the further visual indicator and visual indicator have different visual characteristics.

18. The method of claim 16 wherein the visual indicator comprises a colored indicator.

19. The method of claim 16 wherein the plurality of different discrepancies comprises a recalled medication discrepancy.

20. A non-transitory computer readable medium for a medication inventory management system comprising a medication tray comprising a plurality of partitions defining a plurality of compartments, the medication tray having a tray identifier associated therewith, each compartment for storing a respective medication having a medication identifier associated therewith and each compartment having an open unlidded upper end for access to the respective medication by medical personnel, the non-transitory computer readable medium comprising computer executable instructions that when executed by a processor cause the processor to perform operations comprising:

operating at least one imaging apparatus configured to view the respective medication identifiers through the open unlidded upper ends of the plurality of compartments; and cooperating with the at least one imaging apparatus to determine the tray identifier and medication identifiers of the medication tray;

maintaining in a memory a desired respective medication within each compartment based upon the tray identifier;

determining the respective medication within each of the plurality of compartments based upon the medication identifiers;

determining a discrepancy from among a plurality of different discrepancies between the determined respective medication within each compartment and the desired respective medication within each compartment, and when so generating a display notification comprising an image of the medication tray with a visual indicator corresponding to each compartment determined to have the discrepancy overlaid thereon the image of the medication tray, and text indicating the corresponding discrepancy from among the plurality of different discrepancies with the associated compartment for each compartment determined to have the discrepancy, the plurality of different discrepancies comprising a medication expiration discrepancy and an incorrect medication discrepancy; and displaying the display notification on a display coupled to the processor.

21. The non-transitory computer readable medium of claim 20 wherein the display notification comprises a further visual indicator corresponding to each compartment determined to not have a discrepancy; and wherein the further visual indicator and visual indicator have different visual characteristics.

22. The non-transitory computer readable medium of claim 20 wherein the visual indicator comprises a colored indicator.

23. The non-transitory computer readable medium of claim 2 wherein the plurality of different discrepancies comprises a recalled medication discrepancy.

* * * * *

UNITED STATES PATENT AND TRADEMARK OFFICE
CERTIFICATE OF CORRECTION

PATENT NO. : 11,514,397 B2
APPLICATION NO. : 16/448493
DATED : November 29, 2022
INVENTOR(S) : Wolfe et al.

Page 1 of 1

It is certified that error appears in the above-identified patent and that said Letters Patent is hereby corrected as shown below:

In the Claims

Column 25, Line 2    Delete: "2"
Insert: --20--

Signed and Sealed this
Eighteenth Day of April, 2023

Katherine Kelly Vidal
*Director of the United States Patent and Trademark Office*